US012589133B2

(12) United States Patent
Mohapatra et al.

(10) Patent No.: US 12,589,133 B2
(45) Date of Patent: Mar. 31, 2026

(54) METHODS OF DOWNREGULATING CCL20 GENES FOR TREATMENT OF TRAUMATIC BRAIN INJURIES

(71) Applicant: University of South Florida, Tampa, FL (US)

(72) Inventors: Subhra Mohapatra, Lutz, FL (US); Shyam S. Mohapatra, Lutz, FL (US); Karthick Mayilsamy, Tampa, FL (US); Eleni Markoutsa, Tampa, FL (US)

(73) Assignee: University of South Florida, Tampa, FL (US)

( * ) Notice: Subject to any disclaimer, the term of this patent is extended or adjusted under 35 U.S.C. 154(b) by 1043 days.

(21) Appl. No.: 17/523,009

(22) Filed: Nov. 10, 2021

(65) Prior Publication Data

US 2022/0062382 A1 Mar. 3, 2022

Related U.S. Application Data

(63) Continuation of application No. PCT/US2020/033373, filed on May 18, 2020.

(60) Provisional application No. 62/848,992, filed on May 16, 2019.

(51) Int. Cl.

| | |
|---|---|
| *C07H 21/02* | (2006.01) |
| *A61K 9/00* | (2006.01) |
| *A61K 35/28* | (2015.01) |
| *A61K 38/17* | (2006.01) |
| *A61K 38/19* | (2006.01) |
| *A61K 47/59* | (2017.01) |
| *A61K 47/69* | (2017.01) |
| *A61K 48/00* | (2006.01) |
| *A61P 25/28* | (2006.01) |
| *C07H 21/04* | (2006.01) |

(52) U.S. Cl.
CPC .......... *A61K 38/195* (2013.01); *A61K 9/0019* (2013.01); *A61K 9/0043* (2013.01); *A61K 35/28* (2013.01); *A61K 38/1793* (2013.01); *A61K 47/595* (2017.08); *A61K 47/6931* (2017.08); *A61K 48/0041* (2013.01); *A61P 25/28* (2018.01)

(58) Field of Classification Search
CPC ........................ C12N 15/113; C12N 2310/531
See application file for complete search history.

(56) References Cited

U.S. PATENT DOCUMENTS

| | | | |
|---|---|---|---|
| 7,253,004 B2 | 8/2007 | Vossmeyer et al. | |
| 9,200,276 B2 * | 12/2015 | Hauser .................... | A61P 31/18 |
| 2009/0214484 A1 | 8/2009 | Mironov | |
| 2010/0029748 A1 * | 2/2010 | Massague .......... | A61K 31/7105 435/6.14 |
| 2010/0240730 A1 | 9/2010 | Beigelman | |

| | | | |
|---|---|---|---|
| 2015/0030609 A1 * | 1/2015 | Mohapatra ........... | C12Q 1/6883 435/7.1 |
| 2017/0232120 A1 | 8/2017 | Rangaramanujam et al. | |
| 2020/0061207 A1 | 2/2020 | Mohapatra et al. | |

FOREIGN PATENT DOCUMENTS

WO WO-2011123591 A1 * 10/2011 .............. A61P 31/00

OTHER PUBLICATIONS

Gu et al. (Materials Science and Engineering C 70 (2017) 572-585).*
Galindo et al. (Neurology Research International, 2011, Article ID 564089, 1-9).*
Tang et al. (Mol. Pharmaceutics 2012, 9, 1812-1821).*
Jiang et al. (Cellular and Molecular Neurobiology (2018) 38:1009-1019).*
Pardridge et al. (Adv Drug Deliv Rev. Mar. 30, 2007; 59(2-3)).*
Doskocz et al. (Materials 2021, 14, 4278, 1-20).*
Perez et al. (International Journal of Pharmaceutics 380 (2009) 189-200).*
International Search Report and Written Opinion issued by the International Searching Authority on Sep. 30, 2020 for corresponding international patent application No. PCT/US2020/033373.
International Preliminary Report on Patentability issued by the International Bureau on Nov. 25, 2021 for corresponding international patent application No. PCT/US2020/033373.
Affo et al. CCL20 mediates lipopolysaccharide induced liver injury and is a potential driver of inflammation and fibrosis in alcoholic hepatitis. Gut. Nov. 2014; 63(11): 1782-1792. doi:10.1136/gutjnl-2013-306098.
Jin et al. Astrocyte-derived CCL20 reinforces HIF-1-mediated hypoxic responses in glioblastoma by stimulating the CCR6-NF-KB signaling pathway. Oncogene, Mar. 14, 2018, vol. 37, Issue 23, pp. 3070-3087.
Lu, et al. High-frequency repetitive transcranial magnetic stimulation for treating moderate traumatic brain injury in rats: A pilot study. Experimental and Therapeutic Medicine, Mar. 29, 2017, vol. 13, No. 5, pp. 2247-2254.

(Continued)

*Primary Examiner* — Amy Rose Hudson
(74) *Attorney, Agent, or Firm* — Michele L. Lawson; Shumaker, Loop & Kendrick, LLP

(57) ABSTRACT

Compositions and methods for treating traumatic brain injury (TBI) are presented. Novel dendriplexes are formed from poly(amidoamine) (PAMAM) dendrimers complexed with shRNA encoding DNA plasmids encapsulating shRNA encoding chemokine ligand 20 (CCL20) gene, chemokine receptor 6 (CCR6) gene, or a combination thereof. The dendriplexes are dually administered, both intranasally and intravenously, prior to administration of stem cells, such as human mesenchymal stem cells (hMSCs) for the treatment of traumatic brain injury (TBI). Administration of the dendriplexes prior to stem cell administration resulted in a decrease in neurodegeneration, neuroinflammation, microgliosis and astrogliosis. In addition, a synergistic increase in brain derived trophic factor (BDNF) was shown by administration of the combination of dendriplex and stem cell administration.

9 Claims, 13 Drawing Sheets

(56) References Cited

OTHER PUBLICATIONS

Popovitz et al. Long-Term Effects of Traumatic Brain Injury on Anxiety-Like Behaviors in Mice: Behavioral and Neural Correlates. Frontiers in Behavioral Neuroscience, Jan. 23, 2019, vol. 13, Art. 6, pp. 1-12.

Lim et al. Stabilization of polyamidoamine (PAMAM) dendrimers/sodium dodecyl sulfate complexes via PEGylation. Colloids and Surfaces A: Physicochem. Eng. Aspects 380 (2011) 47-52.

Sharma et al. Effect of mannose targeting of hydroxyl PAMAM dendrimers on cellular and organ biodistribution in a neonatal brain injury model. Journal of Controlled Release 283 (2018) 175-189.

Luong et al. PEGylated PAMAM dendrimers: Enhancing efficacy and mitigating toxicity for effective anticancer drug and gene delivery. Acta Biomaterialia 43 (2016) 14-29.

Das, M., et al., Lateral fluid percussion injury of the brain induces CCL20 inflammatory chemokine expression in rats. J Neuroinflammation, 2011. 8: p. 148.

Das, M., et al., CCL20-CCR6 axis modulated traumatic brain injury-induced visual pathologies. J Neuroinflammation, 2019. 16(1): p. 115.

Das, M., et al., Pioglitazone treatment prior to transplantation improves the efficacy of human mesenchymal stem cells after traumatic brain injury in rats. Sci Rep, 2019. 9(1): p. 13646.

Mastorakos, P., et al., Hydroxyl PAMAM dendrimer-based gene vectors for transgene delivery to human retinal pigment epithelial cells. Nanoscale, 2015. 7(9): p. 3845-56.

Mastorakos, P., et al., Biodegradable brain-penetrating DNA nanocomplexes and their use to treat malignant brain tumors. J Control Release, 2017. 262: p. 37-46.

Das, M., et al., Mesenchymal stem cell therapy for the treatment of traumatic brain injury: progress and prospects. Rev Neurosci, 2019. 30(8): p. 839-855.

Seyhan, A.A., RNAi: a potential new class of therapeutic for human genetic disease. Hum Genet, 2011. 130(5): p. 583-605.

Sah, D.W., Therapeutic potential of RNA interference for neurological disorders. Life Sci, 2006. 79(19): p. 1773-80.

Kannan, S., et al., Dendrimer-based postnatal therapy for neuroinflammation and cerebral palsy in a rabbit model. Sci Transl Med, 2012. 4(130): 130ra46. doi: 10.1126/scitranslmed.3003162.

Kim, I.D., et al., Neuroprotection by biodegradable PAMAM ester (e-PAM-R)-mediated HMGB1 siRNA delivery in primary cortical cultures and in the postischemic brain. J Control Release, 2010. 142(3): p. 422-30.

Lee, J.H., et al., Polyplexes assembled with internally quaternized PAMAM-OH dendrimer and plasmid DNA have a neutral surface and gene delivery potency. Bioconjug Chem, 2003. 14(6): p. 1214-21.

Albertazzi, L., et al., In vivo distribution and toxicity of PAMAM dendrimers in the central nervous system depend on their surface chemistry. Mol Pharm, 2013. 10(1): p. 249-60.

Shakhbazau, A., et al., Use of polyamidoamine dendrimers to engineer BDNF-producing human mesenchymal stem cells. Mol Biol Rep, 2010. 37(4): p. 2003-8.

Win-Shwe, T.T., et al., Effects of PAMAM dendrimers in the mouse brain after a single intranasal instillation. Toxicol Lett, 2014. 228(3): p. 207-15.

Hasan, A., et al., Mesenchymal Stem Cells in the Treatment of Traumatic Brain Injury. Front Neurol, 2017. 8: p. 28.

* cited by examiner

B
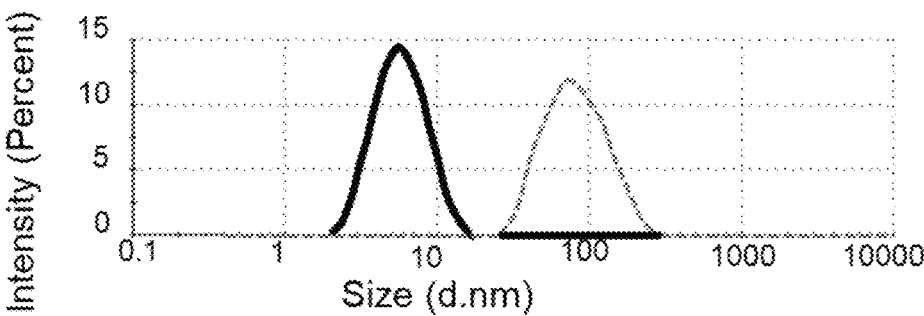
Size distribution by intensity
C
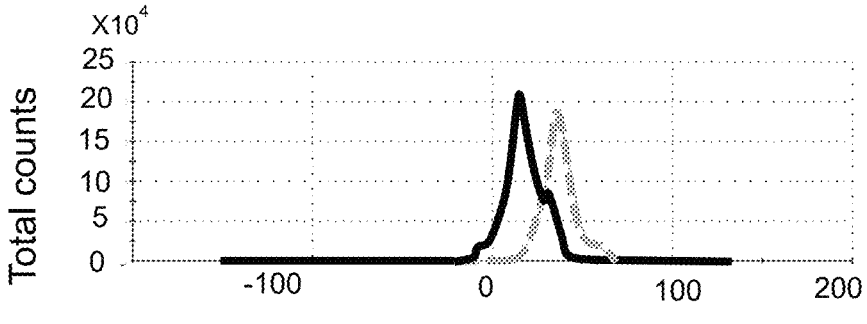
Zeta Potential Distribution
D
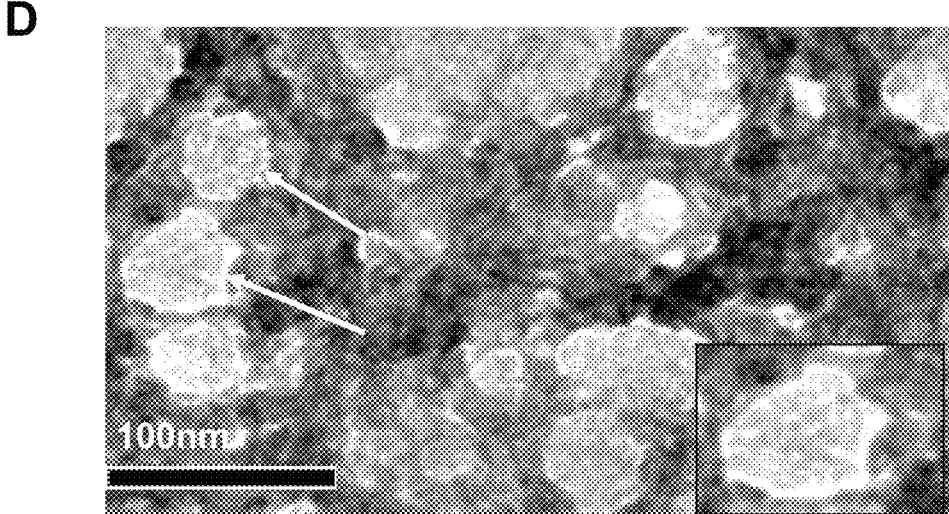
FIG. 1B-D

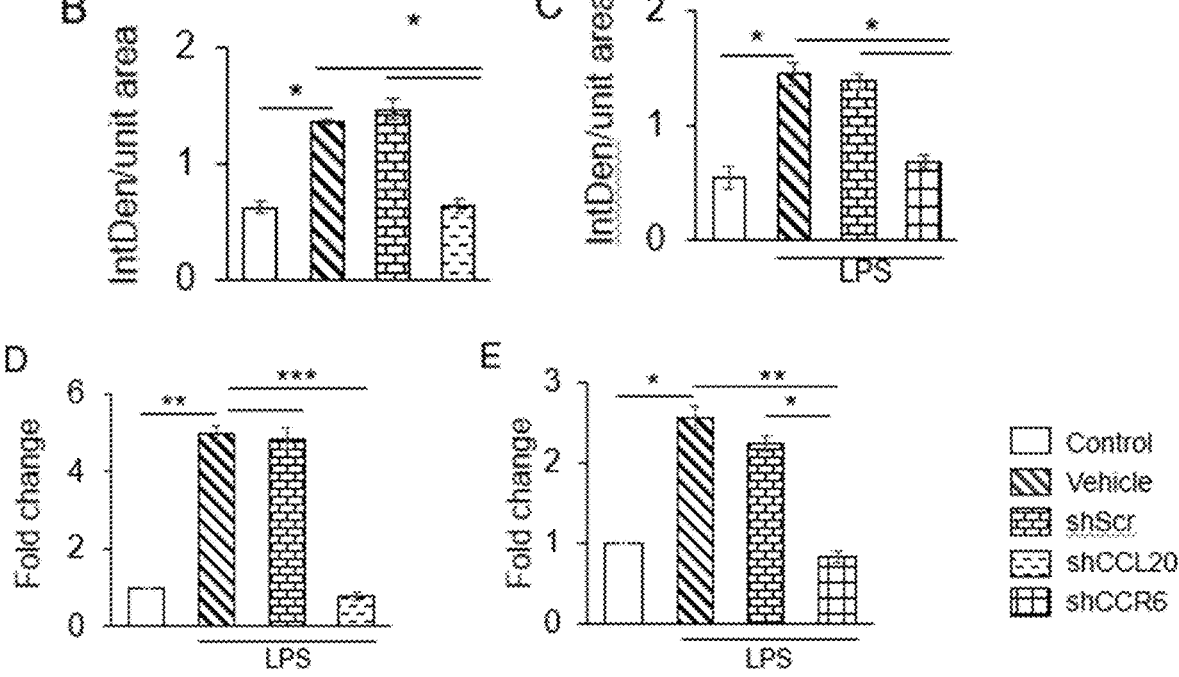
FIG. 2B-E

A
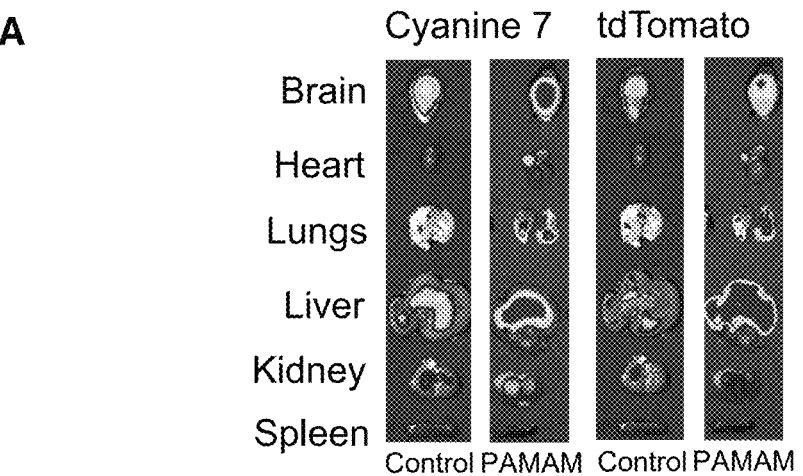
B
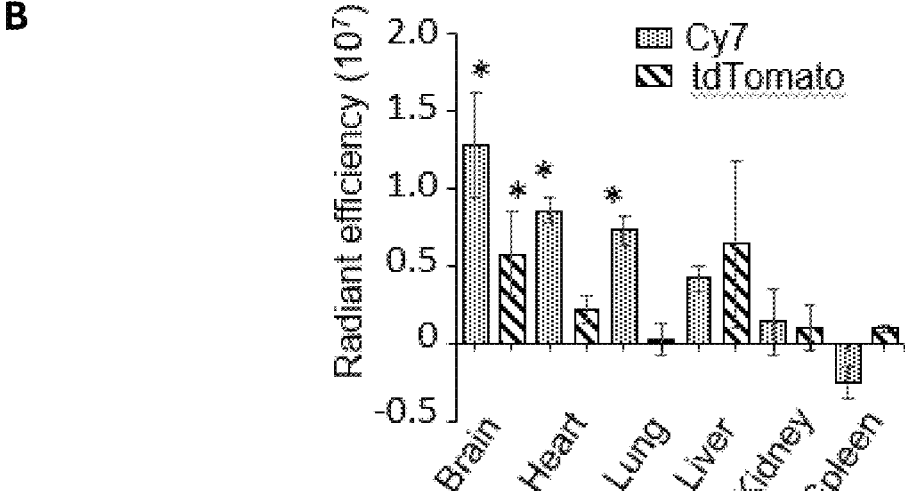
C
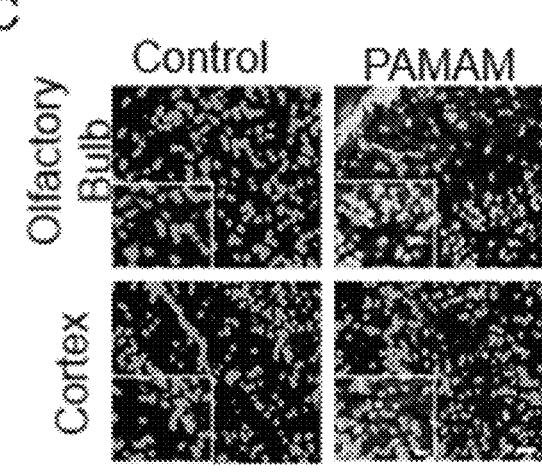
FIG. 3A-C

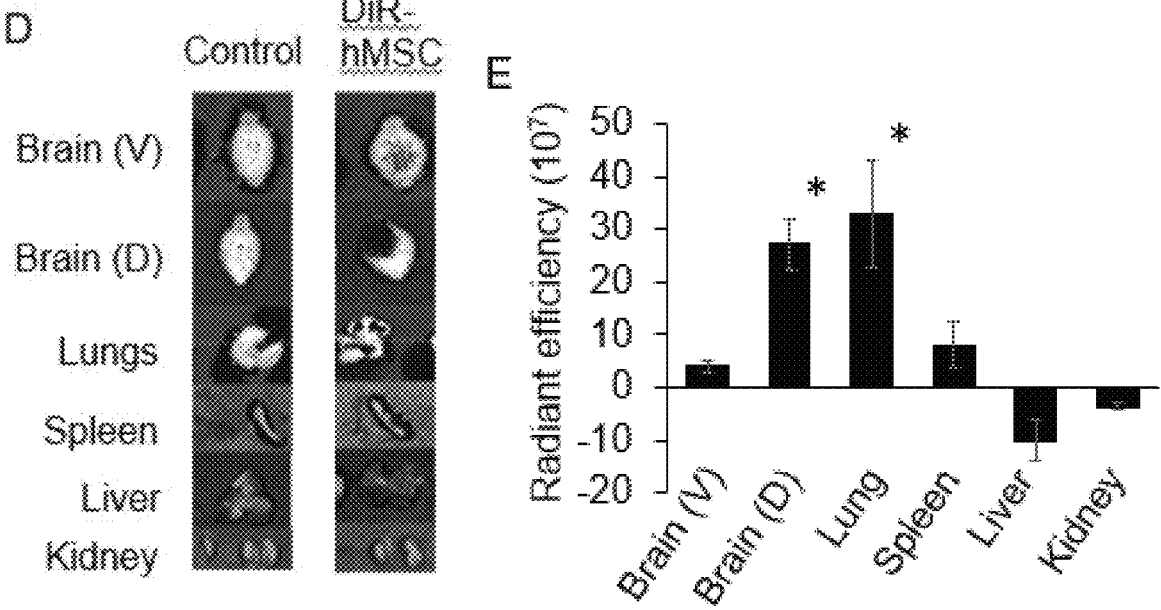
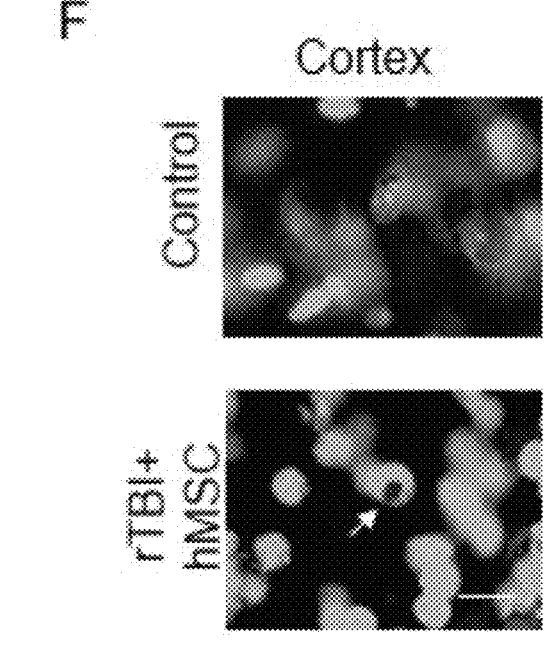
FIG. 3D-F

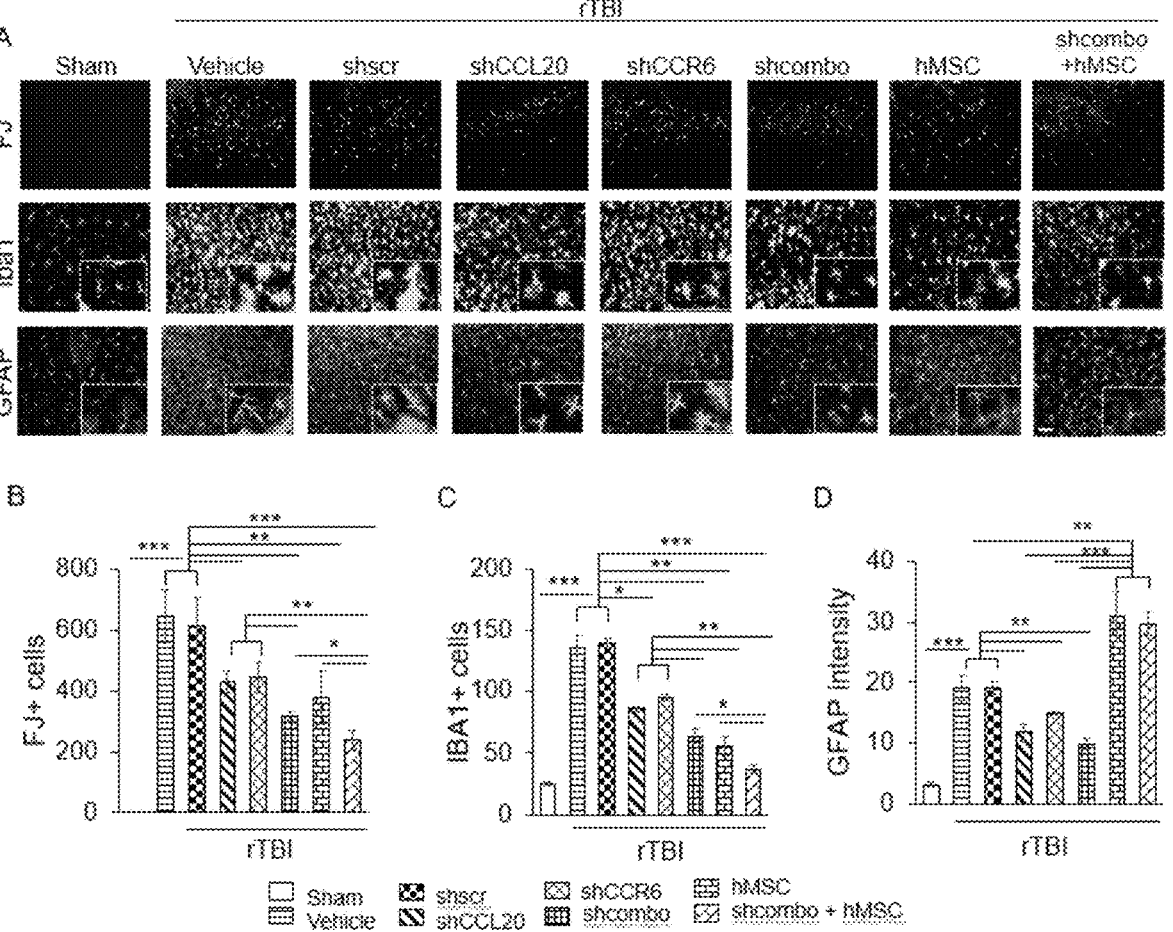
FIG. 4A-D

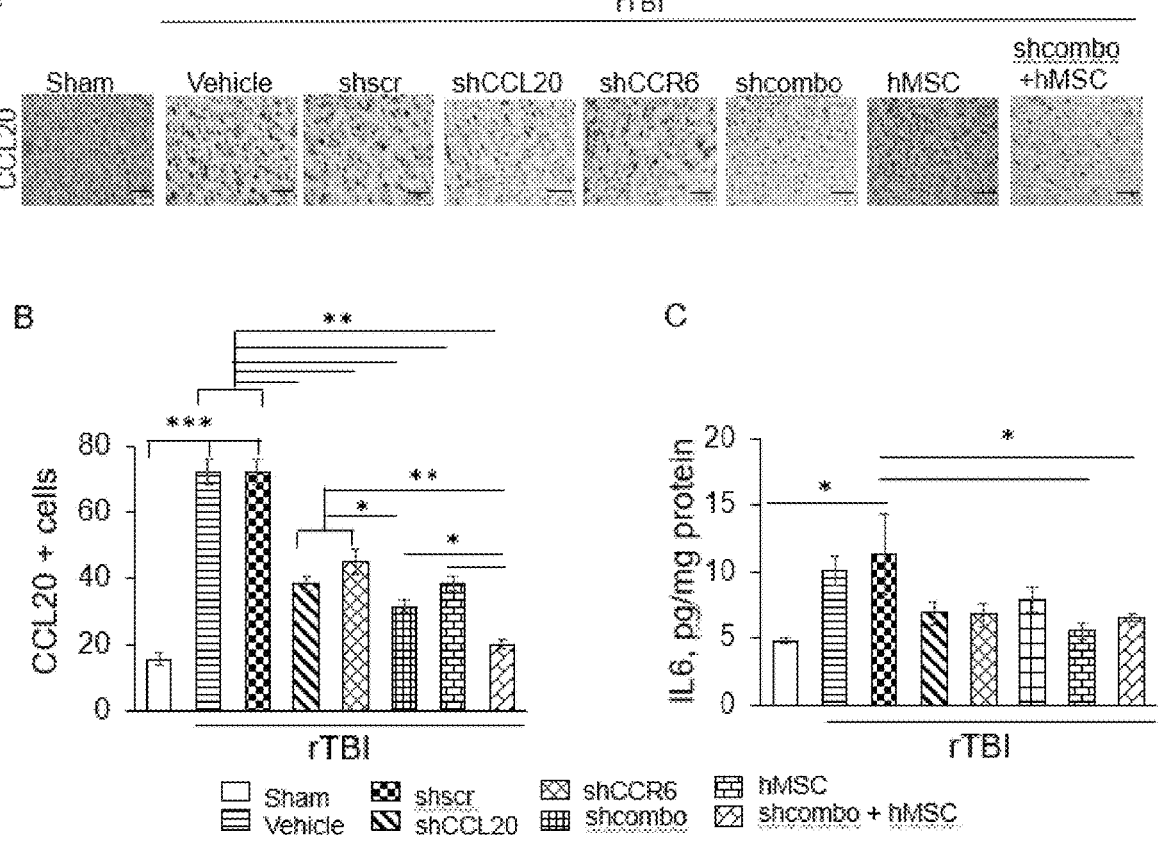
FIG. 5A-C

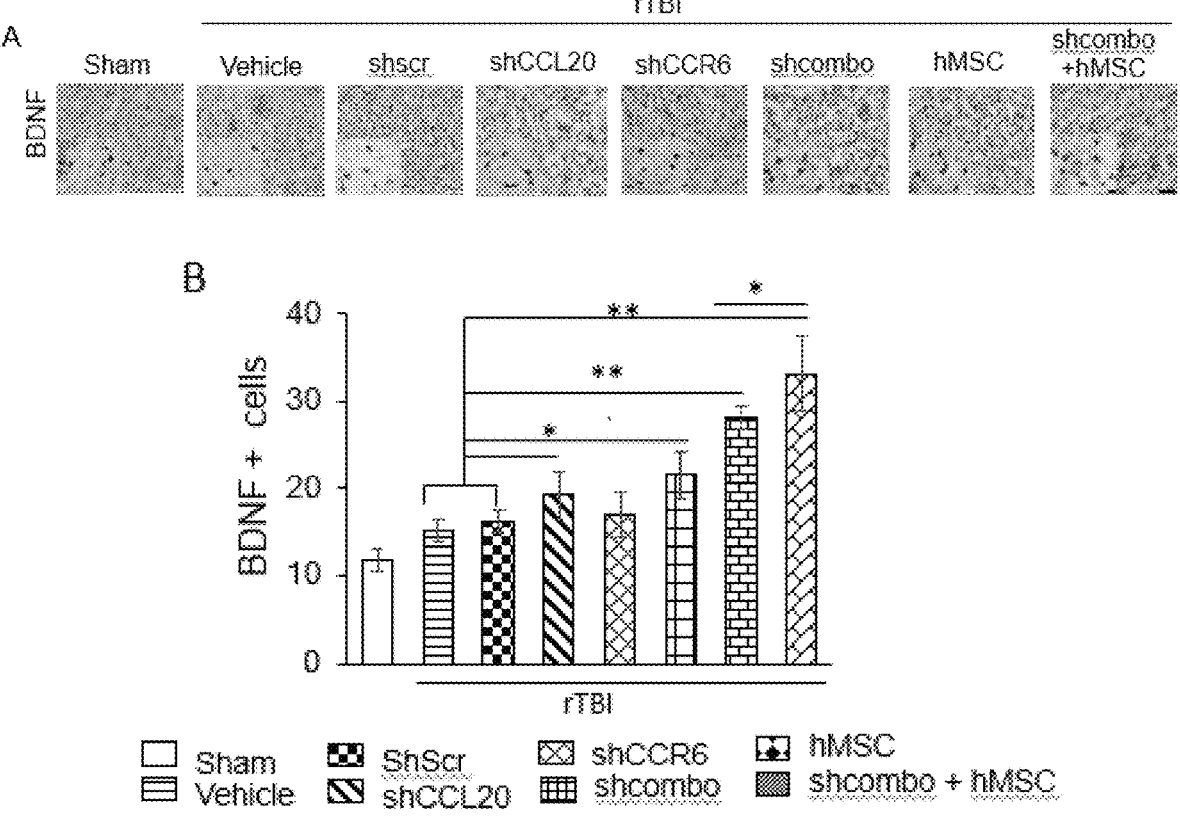
FIG. 6A-B

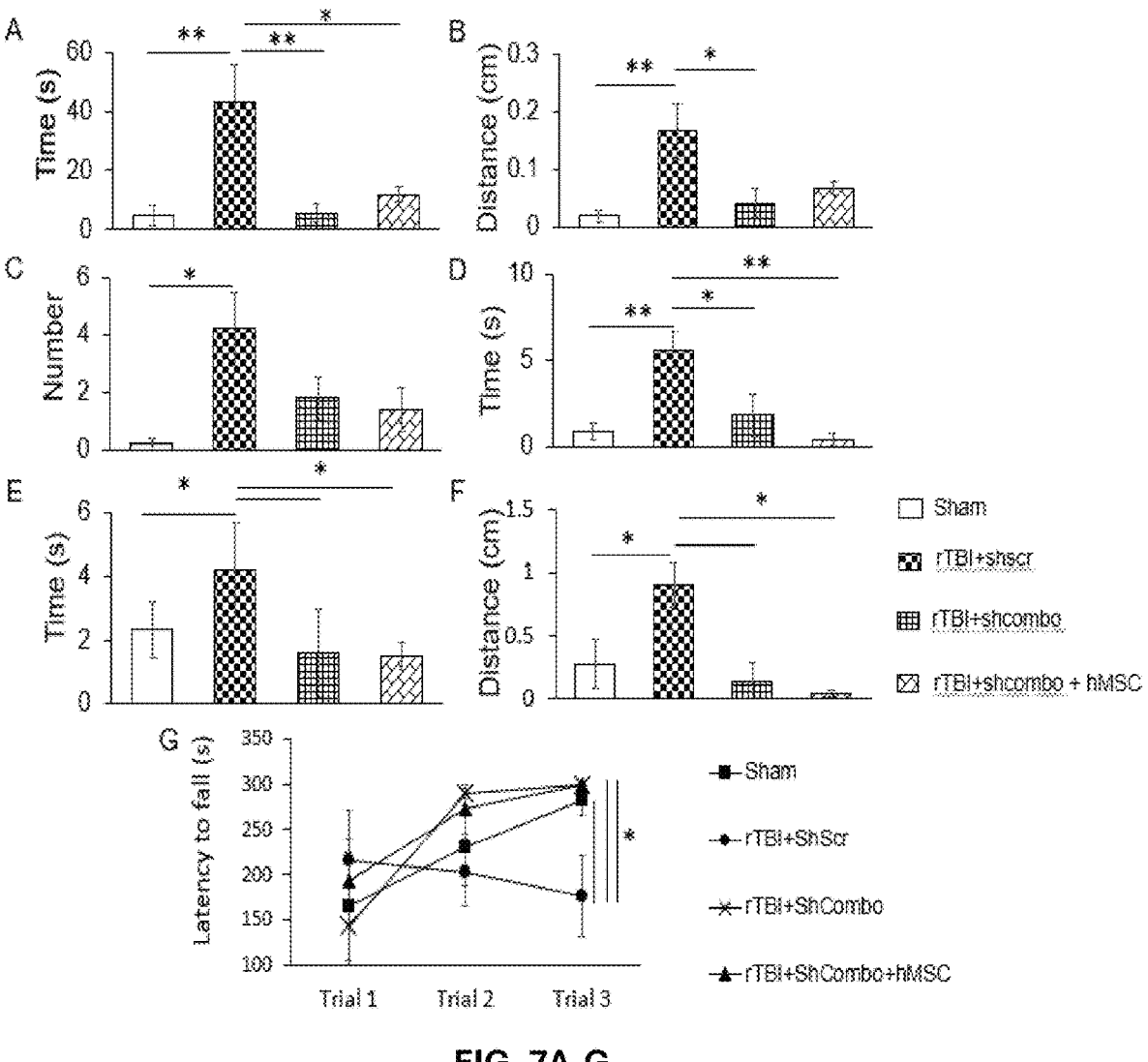
FIG. 7A-G

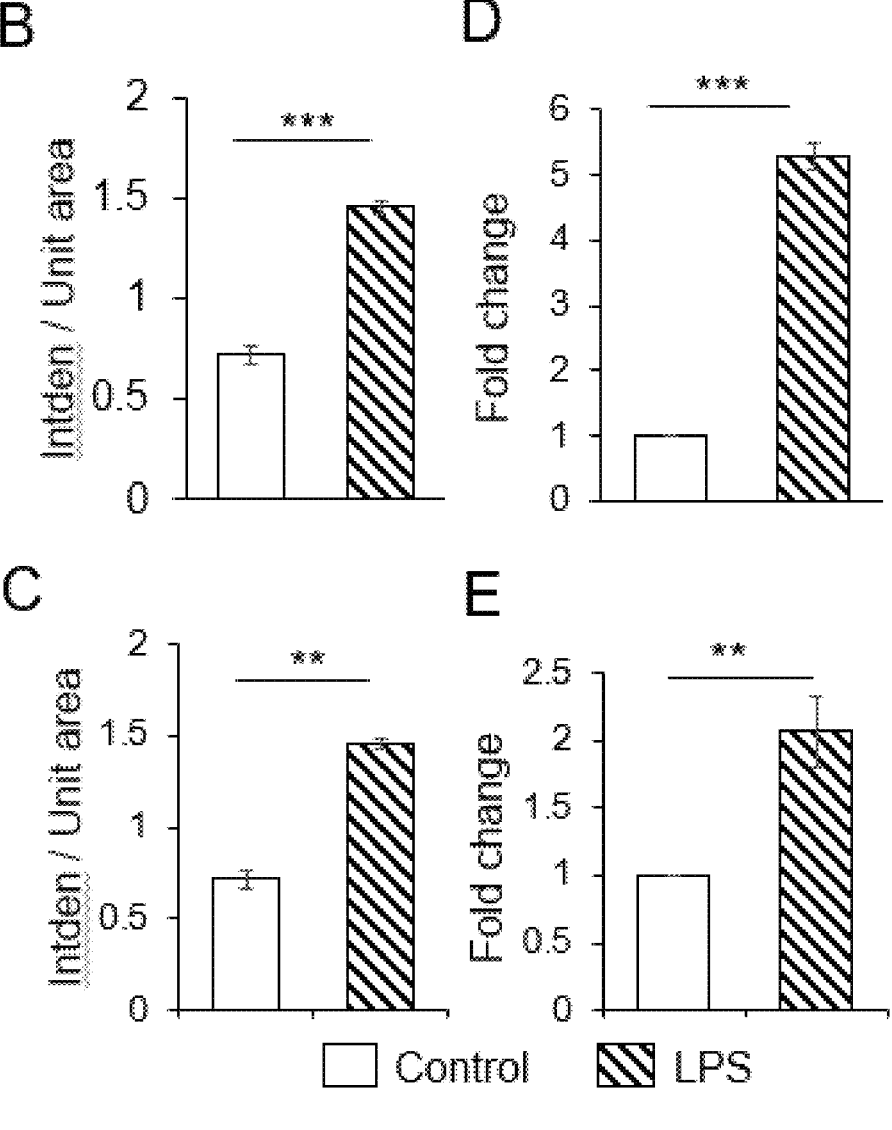
FIG. 8B-E

A
Time in closed arm
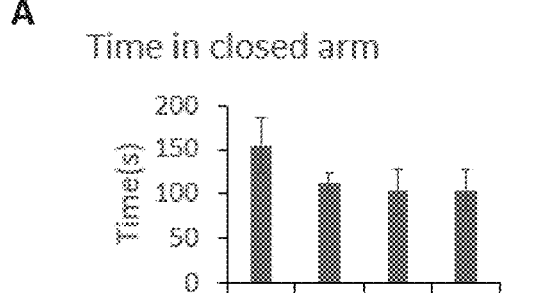
B     Freezing in closed arm
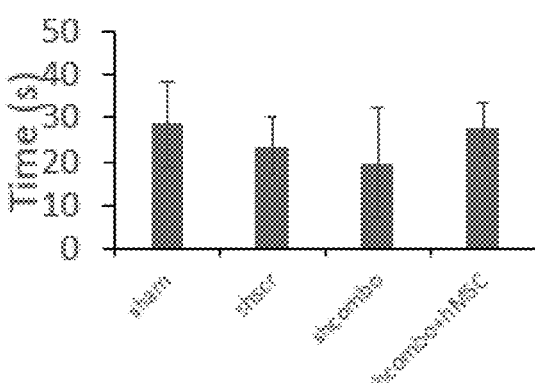
C     Distance in closed arm
(cm)
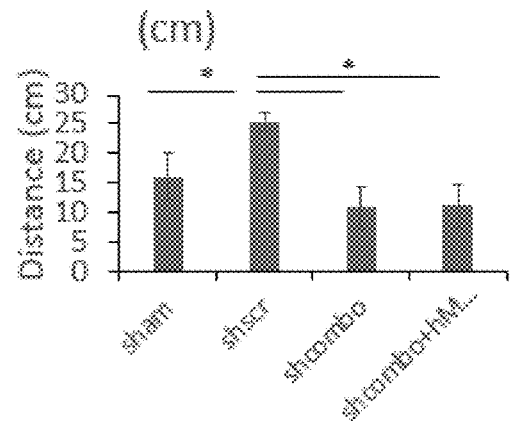
FIG. 9A-C

1

METHODS OF DOWNREGULATING CCL20 GENES FOR TREATMENT OF TRAUMATIC BRAIN INJURIES

CROSS REFERENCE TO RELATED APPLICATIONS

This application is a continuation of an claims priority to International Patent Application No. PCT/US2020/033373, entitled "Methods of Downregulating CCL20 Genes for Treatment of Traumatic Brain Injures", filed May 18, 2020 which claims priority to U.S. Provisional Patent Application Ser. No. 62/848,992, entitled "Methods of Downregulating CCL20 Genes For Treatment of Traumatic Brain Injuries", filed May 16, 2019, the contents of which are hereby incorporated by reference into this disclosure.

FIELD OF THE INVENTION

This invention relates, generally, to treatment of traumatic brain injuries (TBIs). More specifically, it relates to therapeutic agent systems and methods of treatment designed to be administered to patients suffering from symptoms associated with TBIs.

BACKGROUND OF THE INVENTION

Traumatic brain injury (TBI) is one of the leading causes of death and disability among children and young adults in the United States. According to Center for Disease Control and Prevention's 2019 report, in the United States in the year 2014 alone, 56,800 people, including 2,529 children died from TBI and approximately 288,000 people were hospitalized [1]. The most common causes of TBI has been identified as fall, motor vehicle accidents, sports and battlefield or explosion-related injuries. TBI causes considerable cognitive, affective and motor disorders in the survivors [2, 3]. A subset of TBI patients who experience repeated TBI (rTBI) experience post-traumatic stress disorder, suicidal ideation, and cognitive impairment [4, 5]. [6-10]

Typical approaches to treating patients suffering from symptoms associated to TBIs include neurorestorative approaches, such as stem cell therapies, erythropoietin-regulation, and improvements in neurotrophic factors. Some neuroprotective approaches include the administration of calcium channel blockers, corticosteroids, or monoaminergic agonists. Still other physical therapies include the use of environmental enrichment and exercise in an attempt to treat the symptoms associated with TBIs.

Although TBI appears to be a significant public health problem, there is no such single therapy which can address the problem efficiently. The promising preclinical studies eventually failed at the clinical trials [11-15]. Transplantation of mesenchymal stem cells (MSC) has shown promise in regenerating lost tissues following TBI [16-18]. But there are several factors affecting the efficacy of transplanted MSCs, for example, number and quality of transplanted cells, time of transplantation, and also, the proinflammatory microenvironment of the injured parenchyma. The latter play a crucial role in treatment efficacy by promoting death of the transplanted cells [19].

The inventors have previously shown that CCL20 plays a pivotal role in mediating neuroinflammation after TBI [20-22]; that reducing the neuroinflammation by using pioglitazone, a PPARγ agonist, improves the efficacy of transplanted hMSC following TBI [23]; and that silencing CCL20 along with its sole receptor CCR6 reduced the neuroinflammation and increased the efficacy of transplanted hMSCs in a closed head mouse model of rTBI [21]. The inventors have designed nanoparticles to safely and effectively deliver shRNAs against CCL20 and/or CCR6 to silence the genes prior to hMSC delivery.

Given the lack of a single therapy that can effectively treat TBI, what is needed is an administrable therapeutic that can be used to effectively treat TBI in a patient in need thereof. The inventors have discovered that silencing CCL20 along with its sole receptor CCR6 reduced the neuroinflammation and increased the efficacy of transplanted hMSCs in a closed head mouse model of rTBI [21]. The inventors have designed nanoparticles to safely and effectively deliver shRNAs encoding CCL20 and/or CCR6 to silence the genes prior to hMSC delivery.

BRIEF SUMMARY OF THE INVENTION

In an embodiment, a therapeutic system to treat traumatic brain injury (TBI) in a patient in need thereof is presented comprising at least one dendrimer nanoparticle complexed with at least one short hairpin RNA (shRNA)-encoding DNA plasmid to form at least one dendriplex. The at least one shRNA-encoding DNA plasmid may contain at least one shRNA encoding chemokine ligand 20 (CCL20), chemokine receptor 6 (CCR6) or a combination thereof. In some embodiments, the shRNA-encoding DNA plasmid contains at least one shRNA encoding the CCL20 gene and at least one shRNA encoding the CCR6 gene.

In addition, the therapeutic system may further comprise a therapeutically effective amount of stem cells, such as human mesenchymal stem cells (hMSCs). In this embodiment, the hMSCs may be administered after the administration of the at least one dendriplex.

The dendrimer nanoparticle may be a polyamidoamine (PAMAM) dendrimer nanoparticle.

The at least one dendriplex may be about 100 nm.

In another embodiment, a method of treating a traumatic brain injury (TBI) in a patient in need thereof is presented comprising: administering at least one polyamidoamine (PAMAM) dendrimer nanoparticle complexed with at least one short hairpin RNA (shRNA)-encoding DNA plasmid to form at least one dendriplex and administering a therapeutically effective amount of stem cells. The at least one shRNA-encoding DNA plasmid may contain at least one shRNA encoding chemokine ligand 20 (CCL20), chemokine receptor 6 (CCR6) or a combination thereof. In some embodiments, the shRNA-encoding DNA plasmid contains at least one shRNA encoding the CCL20 gene and at least one shRNA encoding the CCR6 gene.

The stem cells may be human mesenchymal stem cells (hMSCs) and the therapeutically effective amount of hMSCs may be administered after the administration of the at least one dendriplex. The at least one dendriplex may be administered both intranasally and intravenously.

The administration of the both the at least one dendriplex and the therapeutically effective amount of stem cells synergistically increases brain derived neurotrophic factor (BDNF) and reduces anxiety induced by TBI in the patient.

In an embodiment, a method of reducing any one of or the combination of neurodegeneration, local and systemic inflammation, microgliosis and astrogliosis in a patient following traumatic brain injury (TBI) is presented comprising: intranasally and intravenously administering at least one polyamidoamine (PAMAM) dendrimer nanoparticle complexed with at least one short hairpin RNA (shRNA)-encoding DNA plasmid to form at least one dendriplex. The at least one shRNA-encoding DNA plasmid may contain at least one shRNA encoding chemokine ligand 20 (CCL20), chemokine receptor 6 (CCR6) or a combination thereof. In some embodiments, the shRNA-encoding DNA plasmid contains at least one shRNA encoding the CCL20 gene and at least one shRNA encoding the CCR6 gene.

In addition, a therapeutically effective amount of stem cells such as human mesenchymal stem cells (hMSCs) may be administered. The administration of the hMSCs may occur after administration of the at least one dendriplex.

The administration of the both the at least one dendriplex and the therapeutically effective amount of stem cells synergistically increases brain derived neurotrophic factor (BDNF)

BRIEF DESCRIPTION OF THE DRAWINGS

For a fuller understanding of the invention, reference should be made to the following detailed description, taken in connection with the accompanying drawings, in which:

FIG. 1B-D is a series of images depicting the characterization of nanoparticles. (B) Size distribution; (C) zeta potential of the nanoparticle before and after complexation with sh-plasmid; (D) TEM image of PAMAM nanoparticle. Arrows indicate dendrimers.

FIG. 2B-E are a series of images depicting CCL20 or CCR6 is downregulated in shCCL20- or shCCR6-IMG cells. (B and C) Histograms representing image J quantitation of CCL20 (B) or CCR6 (C) immunofluorescence calculated as Integrated density/unit area. (D and E) CCL20 (D) or CCR6 (E) gene expression in stable transfected IMG cells as assessed by qPCR. n=3, Data expressed as Mean±SEM, *p<0.05, p<0.005, *p<0.0005.

FIG. 3A-C are a series of images depicting biodistribution of dendriplexes and hMSCs. PAMAM NPs with cy7 labelled or Td tomato complexed plasmid were delivered IN and the mice were sacrificed 72 h post administration. A) Ex vivo images of the explanted organs, B) histogram representing level of Cy7 fluorescence or RFP fluorescence in different organs following 72 hrs of intranasal administration (n=3). C) RFP expression in olfactory bulb (upper panel) and cortex (lower panel) at 72 h after IN delivery.

FIG. 3D-F are a series of images depicting biodistribution of dendriplexes and hMSCs. (D) Representative IVIS images showing biodistribution of DiR-labelled hMSCs in different organs 3 days after rTBI in mice. Low magnification images, scale bar 50μ, inset high magnification images, scale bar 10μ (E) histogram representing level of DiR fluorescence in different organs following intranasal administration of hMSC (n=3). (F) Brain sections from the mice after 3 days of hMSC administration were immunostained with anti-human nuclear antigen (HuNu) antibody. The images confirm the presence of HuNu positive cells in cerebral cortex close to the injury site, red fluorescence, HuNu, Blue, DAPI. *p<0.05.

FIG. 4A-D is a series of images depicting combination of shcombo dendriplex and hMSC significantly reduces neuroinflammation by reducing degeneration of neurons, microgliosis, astrogliosis (A) Representative images of the brain sections; (B-D) histograms showing Image J quantifications of (B), FJ staining, (C), Iba1 immunostaining, or (D) GFAP immunostaining. n=5/group. Scale bar 50μ, inset scale bar, 10u *p<0.05,p<0.005,*p<0.0005.

FIG. 5A-C are a series of images depicting Combination of shcombo dendriplex and hMSC significantly reduces neuroinflammatory cytokine expression. (A) Representative bright field photomicrographs of the brain sections and (B) histogram showing Image J quantification of chemokine CCL20 positive cells in the perilesional area 7 days post rTBI with or without treatments. (C) Serum IL6 was measured from serum samples using murine IL6 ELISA kit from Biogems. Total protein was measured using Bradfors assay. n=5/group, scale bar 50μ *p<0.05,p<0.005,*p<0.0005.

FIG. 6A-B are a series of images depicting Combination of shcombo dendriplex and hMSC significantly increases cerebral BDNF expression. (A) Bright field images showing BDNF expressing cells in the cortex, scale bar 50μ, inset, scale bar 10μ (B) Histogram showing imageJ quantitation of BDNF positive cells in the perilesional cortex. n=5/group, *p<0.05, **p<0.01.

FIG. 7A-G are a series of graphs depicting rTBI-induced anxiety and motor behaviors improve after combination treatment. A-D, histograms showing the behaviors in the OF. Time spent (A), distance traveled (B), number of freezing episodes (C), and time freezing (D) in the center zone of: E,F, histograms showing the behaviors of mice on the EPM. Time spent (E) and distance traveled (F) in the CZ of EPM. G, Line diagram showing the performance of mice on rotarod. OF, open field arena, EPM, Elevated Plus Maze, n=5/group, *p<0.05, **p<0.001.

FIG. 8B-E are a series of graphs depicting LPS increases CCL20 or CCR6 expression in IMG cells. (B and C) Histograms showing CCL20 (B) or CCR6 (C) immunofluorescence (Integrated density/Unit area) as measured by Image J and expressed as Mean±SEM. (D and E) Gene expression of CCL20 (D) or CCR6 (E) was assessed by qPCR. n=3; *p<0.05,p<0.005,*p<0.0005.

FIG. 9A-C are a series of graphs depicting the behavior of mice in the closed arm of the EPM. (A) Time in seconds each mouse type spent in closed arm; (B) Time in seconds each mouse type spent freezing in place in closed arm; (C) distance in centimeters each mouse type traveled in closed arm.

DETAILED DESCRIPTION OF THE INVENTION

Figure 1A:
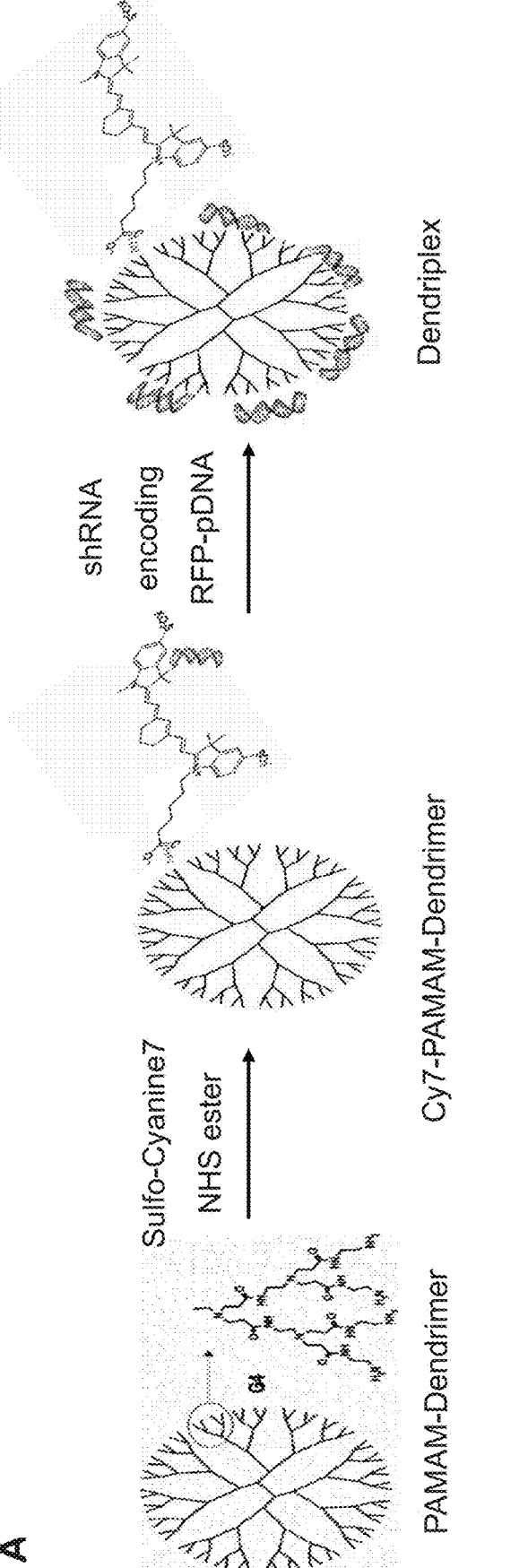
FIG. 1A is an image depicting the preparation and characterization of nanoparticles. (A) A schematic diagram showing the labelling of PAMAM with cy7 and preparation of nano dendriplexes by complexing the PAMAM dendrimer with shRNA encoding plasmid DNA.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined. Where particular values are described in the application and claims, unless otherwise stated, the term "about" meaning within an acceptable error range for the particular value should be assumed. As used herein "about" refers to ±10% of the numerical.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

"Therapeutic agent" as used herein refers to a composition, compound, chemical or extract that can be administered to a subject to treat a brain injury or disorder such as TBI including, but not limited to genes and gene products, stem cells, and small molecule drugs. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof. In some embodiments, one of the therapeutic agents used are shRNAs encoding CCL20 and/or CCR6 delivered to the cell in a DNA plasmid complexed to a dendrimer to form a dendriplex. Subsequent administration by stem cells as a further therapeutic agent is contemplated in some disclosed therapeutic systems.

"Subject" is used to describe an animal, preferably a mammal, more preferably a human, to whom treatment is administered, including prophylactic treatment with the compositions of the present invention. Vertebrate animals include mammals such as humans, primates, canines, felines, bovines, porcines, equines, aves, ruminants, etc. The terms "patient" and "subject" are used interchangeably herein. "Subject" and "patient" are used interchangeably herein.

The term "treatment" or "treating" as used herein refers to the ability to ameliorate, suppress, mitigate, or eliminate the clinical symptoms after the onset of a disease state. Treatment of a brain disorder such as traumatic brain injury (TBI) may include any one or more of the following: amelioration and/or elimination of one or more symptoms associated with TBI, reduction of one or more symptoms of TBI, stabilization of symptoms of TBI, and delay in progression of one or more symptoms of an TBI.

The "therapeutically effective amount" for purposes herein is thus determined by such considerations as are known in the art. A therapeutically effective amount of the therapeutic agent system, nanoparticles, genes, stem cells or any combination thereof is that amount necessary to provide a therapeutically effective result in vivo. The amount must be effective to achieve a response, including but not limited to total prevention of (e.g., protection against) and to improved survival rate or more rapid recovery, or improvement or elimination of symptoms associated with traumatic brain injury and related brain disorders or other indicators as are selected as appropriate measures by those skilled in the art. In some embodiments, the therapeutically effective amount of stem cells administered is at least 1 million stem cells. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Stem cells" as used herein refers to self-renewing cells that are capable of giving rise to phenotypically and genotypically identical daughter cells as well as at least one other final cell type (e.g., terminally differentiated cells).

The term "mesenchymal stem cells" (MSCs) as used herein refers to pluripotent fibroblast-like cells capable of secreting trophic factors. MSCs can be derived from various different tissues including, but not limited to, bone marrow (BM), umbilical cord (UC), adipose tissue, and umbilical cord blood (UCB).

"Administration" or "administering" is used to describe the process in which the therapeutic system, nanoparticles, therapeutic agents, genes, stem cells, or any combination thereof of the present invention are delivered to a patient. The composition may be administered in various ways including parenteral (referring to intravenous, intraarterial, intranasal, topical and other appropriate parenteral routes), among others. Administration will often depend on the disease and level of progression in the afflicted brain.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once per day, at least once every other day, at least 3 times per week, at least twice per week, and at least once per week. In some embodiments, the interval between each administration is less than about 24 hours, such as less than about any of 23, 22, 21, 20, 19, 18, 17, 16, 15, 14, 13, 12, 11, 10, 9, 8, 7, 6, 5, 4, 3, 2, or 1 hour. In some embodiments, the interval between each administration is constant. For example, the administration can be carried out every hour, every two hours, every three hours, every four hours, every 5 hours, every six hours, every seven hours, every eight hours, every nine hours, every ten hours, every eleven hours, or every twelve hours. In some embodiments, the administration can be carried out twice daily, three times daily, or more frequent.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compositions used in the present invention may be administered individually, or in combination with or concurrently with one or more other compositions. Additionally, compositions used in the present invention may be administered in combination with or concurrently with other therapeutics for brain disorders such as TBI.

The compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention and are capable of local and/or systemic administration. Examples include, but are not limited to, phosphate buffered saline, physiological saline, water, and gels. Formulations are described in a number of sources that are well known and readily available to those skilled in the art. For example, *Remington's Pharmaceutical Sciences* (Martin E W [1995] Easton Pennsylvania, Mack Publishing Company, 19^th^ ed.) describes formulations which can be used in connection with the subject invention.

For ease of administration, the subject compositions and therapeutic agents may be formulated into various pharmaceutical forms. As appropriate compositions that may be cited include all compositions usually employed for locally or systemically administering compositions including, but not limited to, parenteral (referring to intravenous, intraarterial, intranasal, and other appropriate parenteral routes). For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution.

An average 40 g mouse has a brain weighing 0.416 g, and a 160 g mouse has a brain weighing 1.02 g, a 250 g mouse has a brain weighing 1.802 g. An average human brain weighs 1508 g, which can be used to direct the amount of therapeutic needed or useful to accomplish the treatment described herein.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

"Short hairpin RNA" or "shRNA" as used herein refers to single stranded RNA molecules that are constructed by connecting sense and antisense strands of an siRNA duplex with a loop sequence thus allowing a single transcript to fold back on a duplex structure upon being transcribed. After transcription, the shRNA molecules are processed into siRNAs by the Dicer enzyme and are capable of suppressing a gene. In an embodiment, the therapeutic agent system described herein knocks down, or silences, the genes CCL20, CCR6 or a combination thereof.

"Dendrimer" as used herein refers to a highly branched synthetic polymer macromolecules capable of being used in delivery of therapeutic agents, such as drugs, in a patient. Dendrimers as used herein refer to nanoparticle dendrimers having a size range of 5-50 nm and certain dendrimers being about 5 nm in some embodiments. Dendrimers are constructed by the successive addition of branching group layers with each branching group layer being a new generation. Dendrimers capable of being used herein include, but are not limited to, Poly(propyleneimine) dendrimers (PPI), Poly(amidoamine) dendrimers (PAMAM), Poly 2,2-bis(methylol)propionic acid (PBisMPA), Poly(benzyl ether) dendrimers (PBzE), poly(lysine) dendrimers (PLL), and polymelamine (triazine) dendrimers. If PAMAM dendrimers are used, any of generations 0-11 (G0-G11) may be used. In some embodiments, PAMAM G4 is used. PAMAM dendrimers generally comprise an ethylenediamine core, a repetitive branching amidoamine internal structure and a primary amine terminal surface.

"Dendriplex" as used herein refers to dendrimers that have been functionalized by the complexation (conjugation) of at least one therapeutic agents and/or genes to deliver genes/gene products and/or therapeutic agents to the brain. In some embodiments, the dendrimers have an shRNA encoding DNA plasmid complexed to the outer surface of the dendrimer. In some embodiments, the shRNA contained within the plasmid encodes chemokine ligand 20 (CCL20), chemokine receptor 6 (CCR6) or a combination thereof. "Combination thereof" refers to at least two shRNAs with at least one shRNA encoding CCL20 and at least shRNA encoding CCR6. Dendriplex size having a range of about 50-200 nm.

"Functionalized" as used herein refers to altering the surface of the dendrimer by physical interactions or chemical conjugation with specific molecules to induce a desired bioresponse or inhibit a potentially adverse reaction while maintaining the functionality of both the dendrimer and the biomolecule. In some embodiments, the dendrimer surface is altered by conjugating or complexing an shRNA encoding DNA plasmid to the surface of the dendrimer.

rTBI induces significant neurodegeneration and tissue loss in the cerebral cortex 7 dpi in mice. Activation of microglia, astrocytes and cytokine production indicates an active inflammatory milieu in the brain post rTBI. To recover from the damage, it is important to prevent the secondary spread of damage as well as stimulate neurogenesis to enhance the recovery process. Treating TBI conditions with drugs has not been successful so far. Drugs like erythropoietin [13, 14] and progesterone [14, 15] showed promise in the preclinical phases but did not succeed in the clinical trials. Similarly, Nimodipine, a calcium channel blocker did not show enough effect on TBI patients [27, 28]. Cyclosporine showed neuroprotection and prevented calcium ion transport to mitochondria in animal models but not in human patients [29], Tirilizad is a lipid peroxidation inhibitor and an approved drug in Europe to treat aneurismal subarachnoid hemorrhage [30, 31], Selfotel, a NMDA antagonist and the first glutamate antagonist to enter in the phase III clinical trial [32], and statin drugs [33], all showed promise in preclinical models but either were not effective in human patients or proved to be unsafe for humans and eventually failed in clinical trials.

Several investigators have shown the regenerative potentials of MSCs after brain injury. These pluripotent cells differentiate and integrate into the damaged cerebral parenchyma and secrete molecules of paramount regenerative potential [16, 17, 19] and thus, has become the focus of current TBI therapeutics.

Here, the inventors observed that rTBI induced neurodegeneration, microgliosis, and production of inflammatory cytokines like CCL20 and IL6 indicating progress towards secondary neurodegeneration and neuroinflammation. Neurodegeneration and microgliosis were reduced by hMSC therapy but astrocytosis and CCL20 production were still high following hMSC therapy indicating their partial effectiveness in the recovery process. CCL20 along with its unique receptor CCR6 induces chemotaxis of dendritic cells, B and T cells [34]. The inventors have shown previously that CCL20 acts both as a peripheral and local immune signaling molecule in the pathogenesis of TBI and non-specific reduction of CCL20 by pioglitazone [35] prior to implantation significantly improved the efficacy of hMSC [23]. Therefore, the inventors developed a nano material-based strategy to silence the CCL20 gene expression in mice in order to enhance the efficacy of hMSCs after rTBI.

Gene silencing by shRNA is a powerful RNAi strategy which offers a safe, target-specific attenuation of protein expression. However, the efficacy of the gene therapy depends on the successful delivery of the gene to the target site [36, 37]. Over years, several delivery strategies have been engineered that enabled the vehicles to efficiently cross the BBB and deliver the moieties to the brain. However, nanoparticle mediated delivery is one of the highly specific and multifunctional strategy that enables us understanding, diagnosing and treating the diseases [38].

The inventors used PAMAM dendrimers to complex the plasmid DNA-forming dendriplexes to efficiently deliver the shRNA to the brain. PAMAM dendrimers have been widely used in the last decade for diagnostic and therapeutic applications mainly due to their efficiency in crossing the BBB [39][40] and delivering drugs to the brain parenchyma [41, 42]. Their unique hyper-branched structure allows for multiple modifications and functionalities as well as for high drug-loading capacity. The amine end of PAMAM polymers is a useful gene therapy tool for brain diseases as it can be easily complexed with DNA or RNA via electrostatic interactions [40, 43]. Even though the knowledge of their toxicological profile is limited, it has been shown that their toxicity increases as the generation increases so G4 PAMAM is considered nontoxic when administered in low doses [44, 45]. Moreover, it has been shown that brain-derived-neurotrophic factor mRNA was upregulated in the hippocampus and cerebral cortex in mice treated with PAMAM-G4 dendrimers [46].

Example 1—Construction of CCL20/CCR6 shRNA Expression Vector

The shRNA target sequence for knocking down CCL20 and CCR6 was constructed using wizard 3.1 software from Invivogen (San Diego, USA). The mammalian multiple miR30-shRNA knockdown vectors for downregulating CCL20 or CCR6 were purchased from Vector Builder (VectorBuilder Inc, Chicago, USA). Each vector is encoded with 4 inserts of shRNA (CCL20 or CCR6) sequence with (pRP[miR30-shRNA]-Neo-CMV>TurboRFP) CMV promoter, turbo RFP reporter and ampicillin as selectable marker gene. Similarly, a control plasmid with four scramble sequences was also constructed with a similar vector backbone. The plasmids were cloned and amplified in DH5alpha competent cells. The plasmids for carrying out the in vitro and in vivo studies were isolated using a mega preparation plasmid isolation kit from Qiagen (Maryland, USA).

Example 2—Dendriplex Preparation, pDNA Conjugation and Characterization

Polyamidoamine (PAMAM) dendrimer, generation 4 (14215 MW) with 64 surface amine groups, was purchased from Dendritech Inc. (Midland, MI, USA). The average hydrodynamic diameter of the dendrimer was 40 nm with two different peaks at 5 and 100 nm. In order to reduce the size and polydispersity index of the dendrimer stock, the sample was subjected to 3 consecutive cycles of extrusion through polycarbonate membranes of different pore-sizes (200 nm, 100 nm and 50 nm). The average size of the final sample was 5 nm with 0.150 polydispersity index.

Figure 2A:
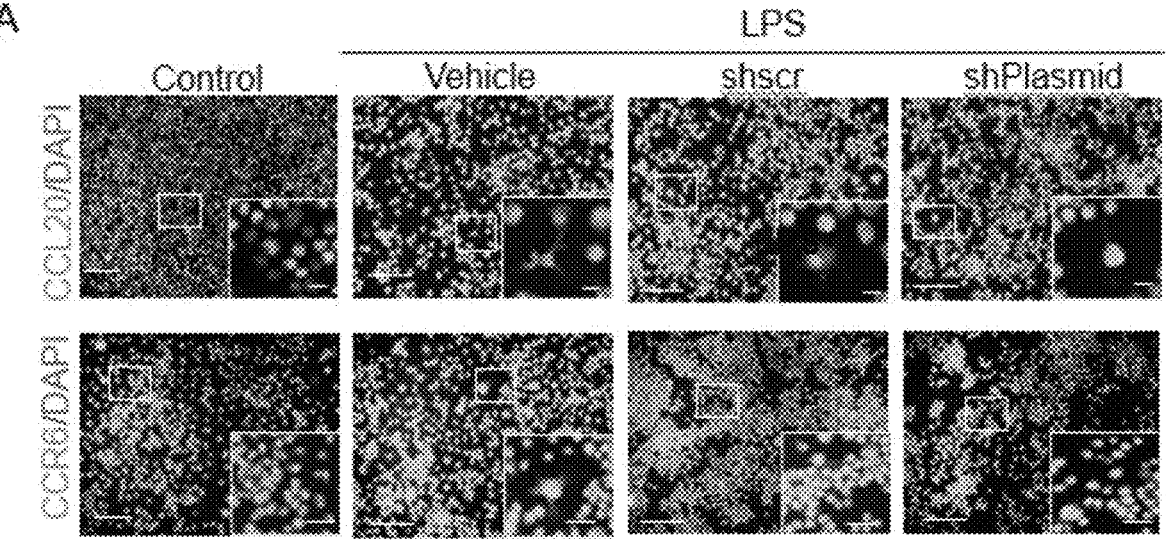
FIG. 2A is a series of images depicting CCL20 or CCR6 is downregulated in shCCL20- or shCCR6-IMG cells. (A) Representative immunofluorescence images showing CCL20 or CCR6 immunostaining in IMG cells stably transfected with scramble (shScr)-dendriplex or shPlasmid-dendriplex (upper panel, shCCL20, lower panel, shCCR6). Low magnification images, scale bar 50μ, inset high magnification images, scale bar 10μ.
Figure 8A:
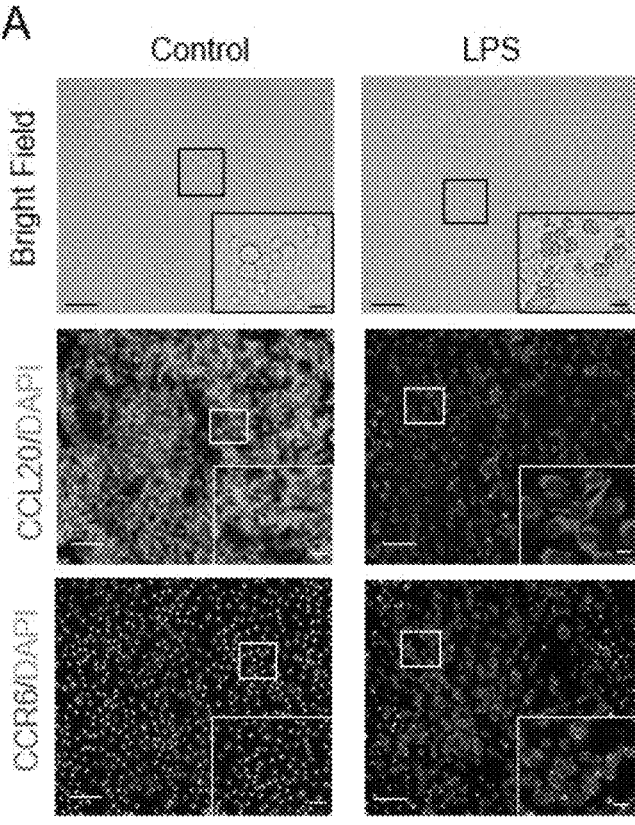
FIG. 8A is a series of images depicting LPS increases CCL20 or CCR6 expression in IMG cells. (A) Representative bright field or immunofluorescence images showing LPS induced activation (upper panel), CCL20 (middle panel) or CCR6 (lower panel) induction in IMG cells in vitro. Low magnification images, scale bar 50μ, inset high magnification images, scale bar 10μ.

Cy-7 labeled dendrimer was prepared through one step reaction as described previously (FIG. 2A) [24, 25]. Briefly, 5 mg of amino-terminated PAMAM dendrimer reacted with 125 g of sulfo-Cyanine 7 NHS ester in 2 ml distilled water overnight at 4° C. The non-conjugated dye was removed by dialysis against pure DI water (membrane MWCO=2 kDa) for 24 h.

PAMAM dendrimer and TurboRFP-pDNA expressing shRNAs, prepared as in Example 1, were complexed via electrostatic interactions to form PAMAM/DNA dendriplexes. The plasmid DNA-dendrimer complexation was achieved by adding plasmid DNA to dendrimer, at a final nitrogen-to-phosphate (N/P) ratio of 10, followed by vigorous vortexing for 1 minute. The average size and $\zeta$-potential of the dendrimer complexes were measured in ultrapure water by dynamic light scattering (Malvern Instruments, Southborough, MA). The nanoparticles were also imaged using high resolution transmission electron microscopy (TEM, Tecnai F20, NREC, USF).

Preparation and Characterization of Dendriplex Nanoparticles

As discussed previously, PAMAM G4 dendrimer was first labeled with Cy-7 utilizing the amine groups on the dendrimer surface and then complexed with shRNA encoding plasmid DNA (FIG. 1A). The successful DNA/dendrimer complexation was confirmed using agarose gel electrophoresis. The average size and ζ-potential of the dendrimer and dendriplex were measured in ultrapure water using zetasizer. FIG. 1B shows that the initial average hydrodynamic diameter of PAMAM dendrimer was 5 nm (broken line) and after complexation with DNA the diameter shifted to 50 –200 nm with an average size of 100 nm (solid line) indicating the successful dendriplex formation. The ζ-potential of the dendrimer was decreased from +35 to +17 after DNA complexation indicating that the amine groups on the surface of the dendrimer were successfully complexed with DNA (FIG. 1C). TEM imaging further confirmed the size and morphology of the dendriplex (FIG. 1D).

Example 3—In Vitro Studies

Cell Culture and LPS Induction

Murine microglial cells (IMG) and human mesenchymal cells were cultured following established methods. Stable transfected cell lines with CCL20 or CCR6 genes silenced were generated by transfection of IMG cells with shCCL20/shCCR6 plasmids using dendrimer and selected the colonies using neomycin. IMG or stable transfected IMG cells expressing CCL20 or CCR6 shRNAs were activated with 100 ng/ml LPS. Cells were fixed with 4% PFA for Immunocytochemistry study and RNA was isolated for gene expression study.

CCL20 and CCR6 Expressions were Downregulated in IMG Cells Stably Transfected with Sh-Dendriplexes Stably transfected IMG cell lines were established in order to study the efficacy of the shCCL20 and shCCR6 plasmids complexed with dendrimers. The established IMG cell lines expressing scramble shRNAs (shScr-IMG), shCCL20 (shCCL20-IMG) and shCCR6 shCCR6-IMG) were activated by challenging with 100 ng/ml LPS for 24 h.

Immunocytochemical staining and imageJ quantitation show that CCL20 or CCR6 expressions increased in vehicle or shscr-IMG cells. On the other hand, shCCL20-IMG or shCCR6-IMG cells did not show elevated CCL20 (FIG. 2A, upper panel, B) or CCR6 (FIG. 2A, lower panel, C) expressions. In addition, the gene expression data shows that in the vehicle or shscr-IMG cells, LPS induced substantial levels of CCL20 (FIG. 2D) or CCR6 (FIG. 2E) gene expressions while the expression levels were significantly less in shCCL20-IMG or shCCR6-IMG cells.

IMG cells have been shown to produce both CCL20 and CCR6 upon activation by LPS. By stable transfection using shCCL20 or shCCR6 complexed with PAMAM dendrimers (shCCL20/shCCR6), the cells do not express CCL20 or CCR6 upon LPS induction, thus, showing the efficacy of the nanoparticles in delivering and silencing the CCL20 or CCR6 genes.

Example 4—In Vivo Studies

Animal Experiments

All animal procedures were conducted in accordance with the NIH guidelines for the Care and Use of Laboratory Animals and approved by the Institutional Animal Care and Use Committee of the University of South Florida. Male C57BL/6 mice 14-16 weeks old were housed in the animal facility on a 12 h light-12 h dark cycle with food and water available ad libitum.

Male C57BL/6 mice were anesthetized with continuous flow of a mixture of 2% of isoflurane. A closed head rTBI was induced, as described [21]. Briefly, using a controlled cortical impactor with a tip diameter of 5 mm, a velocity of 5 m/s, impact depth of 1.5 mm and 200 ms dwell time, five hits were delivered with 48 h between hits, i.e. injuries were experienced on days 0, 2, 4, 6 and 8. Animals were allowed to survive in their home cage for 7 days after the final TBI. Either Cy7 labeled-tdTomato conjugated or shRNA (shCCL20/shCCR6 or combo) conjugated dendrimers were administered simultaneously via both intra-nasal (i.n.) and intra-venous (i.v.) routes after each of the $3^{rd}$, $4^{th}$ and $5^{th}$ TBI, i.e. on days 4, 6 and 8. One million hMSCs, either DiR labeled or unlabeled, were administered via i.n. route after the final dendriplex treatment. Alternatively, the stem cells may be administered via i.v. route. IVIS imaging was performed on explanted organs using appropriate filters. Animals were deeply anesthetized with euthasol (150 μg/ml, i.p.). Blood was collected for serum isolation and the animals were perfusion-fixed with 4% PFA. Brains were harvested and processed for immunostaining.

Open Field (OFT), Elevated Plus Maze (EPM) and Rotarod Tests

Upon receiving, the animals were acclimated to the vivarium for 7 days and handled for another 7 days. During handling, animals were exposed to the experimental room for at least 3 days to eliminate any non-specific stress. During experimentation, animals were exposed to open field arena (OF) or elevated plus maze (EPM) for 7 mins. Activities in the OF or on EPM for last 5 min were recorded by a movie camera and analyzed with Anymaze software. Motor coordination of mice was tested on a Rotarod rotating with an initial speed of 4 rpm which gradually increased up to 40 rpm for a maximum duration of 5 minutes.

ELISA and Histopathological Experiments

ELISA was performed from serum samples using a murine interleukin 6 (IL6) ELISA kit from Biogems (Westlake Village, Ca, Cat #BGK08505) following manufacturer's instructions. Fluoro-jade histochemistry (FJ), immunofluorescence or immunoperoxidase staining was performed on 30μ cryosections. Sections were visualized and images were taken with Olympus X71 microscope using appropriate filters. All immunohistological images were quantitated using ImageJ as described previously [26].

Statistical Analysis

All data are presented as mean±Standard Error of Mean (S.E.M.). Statistical significance was evaluated by ANOVA if not mentioned otherwise. A p value of less than 0.05 was considered statistically significant for all comparisons.

Results

Biodistribution of tdTomato Conjugated Cy7 Labeled Dendriplexes in rTBI Mice Prior to in vivo efficacy studies, the inventors examined the biodistribution of the dendriplexes in rTBI mice. For this purpose, the cy7 labelled dendrimers or tdTomato plasmid complexed dendrimers expressing red fluorescent protein and administered both intranasally and intravenously in a subset of rTBI mice. The IVIS images show cy7 fluorescence 72 h post administration in brain, lungs, liver and kidney indicating the distribution of the complex to these organs (FIG. 3A, B, C). The fluorescence of cy7 labelled dendrimer was found more in brain and liver when compared to other organs. The expression of tdTomato plasmid complexed with PAMAM dendrimers was observed in rTBI mice after 72 h of administration. IVIS imaging shows that the expression was more pronounced in brain and liver compared to other organs (FIG. 3A, B). Cryosections of brain show the tdTomato plasmid expression in the olfactory bulb as well as in the cortex confirming the intranasal delivery (FIG. 3C).

Biodistribution of Intranasally Delivered hMSCs in rTBI Mice

The intranasal administration of DiR-labeled hMSCs to the brain was assessed using IVIS imaging system. DiR fluorescence was observed in the brain and lungs 7 days after the administration (FIG. 3D). The radiant efficiency of DiR signal was significantly higher in the dorsal part of the brain (Cerebral cortex) and in the lungs indicating the intranasally administered cells were present in these areas after 7 days of administration (FIG. 3E). The brain sections were immunostained with anti-human nuclear (clone 235-1) antibody (HuNu) to confirm the presence of hMSCs in the brain. The presence of HuNu-DAPI double positive nuclei in perilesional cerebral cortex confirms the presence of hMSCs in that area 7 days post administration (FIG. 3F).

Sh-Dendriplex-hMSC Combination (shCombo+hMSC) Treatment Reduces Neurodegeneration, Neuroinflammation, Microgliosis and Astrogliosis after rTBI in Mice rTBI induced neurodegeneration as observed in the brain 7 dpi. The FJ staining clearly shows the FJ positive degenerating cells in the cerebral cortex close to the impact site of the rTBI mice. The FJ fluorescent images as well as the Image J quantitation show that the number of FJ positive neurons significantly increased in the vehicle treated or shScr treated mice following rTBI. On the other hand, in shCCL20, shCCR6 or shCombo treated mice, the number of FJ cells decreased as compared to vehicle or shScr mice. The number of FJ positive neurons decreased even more in hMSC or shcombo+hMSC treated mice. The number of FJ positive neurons in these two groups significantly decreased from the shCCL20 or shCCR6 treated mice. This observation clearly indicates the efficacy of shcombo or shcombo+ hMSC therapy over the therapies using single sh-dendriplexes such as shCCL20 or shCCR6 (FIG. 4A upper panel, B).

In addition to neurodegeneration, rTBI in mice causes neuroinflammation and local and systemic cytokine expression. The primary damage due to rTBI leads to activation of microglia. Significant microgliosis was observed after rTBI in vehicle or shscr groups as compared to sham. Immunostaining showed significant increase in number and staining intensity of Iba1 positive microglial cells around the injury site of the cortex in these groups. In shCCL20 or shCCR6 groups number of Iba1 positive cells decreased but in shCombo treated mice the number decreased even more. shcombo+hMSC group showed maximum decrease in number and Iba1 staining intensity among all treatment groups. The morphology of the microglia was also changing to more resting microglial morphology as observed in sham animals (FIG. 4A middle panel, C). Thus, shcombo+hMSC was the most effective therapeutic strategy to reduce the microglial activation after rTBI.

Significant upregulation of GFAP expression after rTBI was observed as compared to sham. In the vehicle or shscr, the GFAP expression was increased as well as the astrocytes were enlarged, and crossed their territorial boundaries. This reactive gliosis was reduced in shCCL20, shCCR6 or shcombo treated mice. In these groups, intensity of GFAP immunoreactivity decreased significantly (FIG. 4A lower panel, C). On the other hand, hMSC or shcombo+hMSC groups showed increase in GFAP positive astrocytes and overall GFAP immunoreactivity. The hMSC induced astrocytosis has been reported previously [23]. In this study also, the inventors observed astrogliosis after hMSC administration but a closer look into the structure of the astrocytes show that the cells' morphology is quite different that activated ones. The astrocytes in these groups are star shaped, maintaining their territorial boundaries indicating their reduced-activated status (FIG. 4A lower panel, C).

In rTBI mice these particles successfully carried the tdTomato plasmid to the brain and expressed the red fluorescent protein in the brain parenchyma. The inventors delivered shCCL20/shCCR6 or a combination of the two intranasally and intravenously following rTBI. This dual delivery approach was taken considering the systemic inflammatory response evoked by TBI. Using dual delivery, the inventors successfully silenced the local as well as systemic CCL20 and CCR6 production following rTBI. The approach was effective in creating a favorable environment for the hMSCs to produce their effect. As shown in FIGS. 4 and 5A, treatment with combined shRNA prior to hMSC transplantation reduced the neurodegeneration, microgliosis and brought the CCL20 level almost to the sham level. Also, these reductions were significantly lower than the level of only hMSC treated group. Thus, shCCL20/CCR6 is efficacious in reducing the inflammatory microenvironment, thereby creating a favorable environment for the hMSCs to produce their effects. This treatment also reduced IL6 significantly, the mechanism of which needs further investigation.

Astrocytes are an important cellular component which maintains the structure and functions of the central nervous system. They are essential for neuronal survival [47] and when the brain is injured they become reactive forming glial scar [48] restricting the spread of damage [49]. Astrocytes can be neuroprotective or neurotoxic [48, 50]. MSCs release chemokines which activate surrounding astrocytes to facilitate tissue repair [49, 51]. The inventors observed that hMSC or shCombo+hMSC treatments increased GFAP immunoreactivity in the brains after rTBI. But they did not observe any glial scar formation in these brains. The astrocytes in these groups maintained their territory all over the cortex. It is possible that astrocytosis in the hMSC [49, 51] or shCombo+hMSC treated animals is actually neuroprotective or regenerative. More study is needed to elucidate the exact mechanism of astrocytes under the present conditions.

Shcombo+hMSC Treatment Alters CCL20 and IL6 Expressions after rTBI in Mice

The inventors have shown previously that expression of CCL20 is one of the important neuroinflammatory events occurring 48 h after TBI in the brain [20]. Here, after 7 days of final rTBI, there was significant increase in CCL20 positive cells in the cortex of the vehicle or shscr treated mice, whereas the shCCL20 dendriplex treated animals showed significant decrease in CCL20 expression in rTBI mice brain. shCCR6 treated animals also showed significant decrement in CCL20 expression in the cerebral cortex. The shcombo treated group showed more reduction in CCL20 expression when compared to vehicle or shscr groups or to shCCL20 or shCCR6 groups (FIG. 5A,B). In comparison with all other treatment groups, shcombo+hMSC responded the most in terms of decreasing the expression of CCL20. IL6 is important inflammatory mediator in rTBI. IL6 ELISA from the serum samples of mice of different treatment groups indicate that in the shscr treated groups IL6 increased significantly as compared to sham animals. However, IL6 expression was significantly reduced in hMSC or shcombo+hMSC groups compared to shscr group. The IL6 levels in the shCCL20, shCCR6 or shcombo showed a strong tendency toward reduction but was not statistically significant.

Shcombo+hMSC Treatment Increases BDNF Expression in the Cerebral Cortex

BDNF is an important neurotrophin supporting neurogenesis in the brain. In this study, BDNF expression in the brain did not significantly change in vehicle or shscr groups after rTBI as compared to sham. The number of BDNF expressing cells around the injury site in the shCCL20 group significantly increased over vehicle or shscr group. hMSC administration significantly increased the number of BDNF cells in the cortex, the number being highest in the shcombo+hMSC treated group. In the shcombo+hMSC group the BDNF positive cell number was significantly higher than that in the hMSC group (FIG. 6A,B). This observation clearly shows that shcombo treatment prior to hMSC administration affects the hMSC treatment outcome in a positive manner.

Probably the most encouraging observation lies in the increase of BDNF in the treatment groups. Silencing CCL20 and CCR6 together as well as hMSC transplantation individually increased BDNF, but prior silencing of CCL20 and CCR6 by treatment with shCombo synergistically increased BDNF above all other treatment groups. This is important because this observation indicates that at this early stage after the injury, the brain is already preparing for the reparative process. At this time point, the inventors did not determine any active neurogenesis in the brain of the treated animals, but the increase in BDNF is a strong indication of the process to be started.

Shcombo+hMSC Treatment Improves the rTBI-Induced Behavioral Deficiencies in Mice Anxiety like behaviors in a novel environment were tested in the OF or EPM. In the OF, shscr treatment after rTBI mice spent significantly longer time (FIG. 7A) in the center zone (CZ) and covered longer distance (FIG. 7B) compared to sham animals. Following shcombo or shcombo+hMSC treatments after rTBI the time spent and distance traveled in the CZ were reduced to the level of the sham animals (FIG. 7A, B). In the CZ, shscr treatment after rTBI mice froze significantly more compared to sham mice. Both the numbers of freezing episodes (FIG. 7C) and the time of freezing (FIG. 7D) were significantly higher in rTBI mice treated with shScr. The freezing behavior reduced in rTBI mice after shcombo+hMSC treatments (FIG. 7C,D). On the EPM, while all animals spent significant time in the closed arm, rTBI mice treated with shscr covered significantly longer distance in the closed arm compared to sham and shcombo or shcombo+hMSC treatment groups (FIG. 9A-C). On the other hand, shscr animals visited the CZ more often than the sham animals, and spent significantly longer time and covered longer distance in the CZ of EPM compared to sham and this behavior was reduced significantly in the shcombo or shcombo+hMSC treatment groups (FIG. 7E,F). To test the motor coordination, mice were tried 3 times on the rotarod. Sham animals along with the shcombo and shcombo+hMSC treated groups showed significant improvement in the fall latency over the rTBI+ shscr animals (FIG. 7G).

In the early phase of the disease, TBI patients show behavioral abnormalities, like judgment issues, increased risk taking, and depression [52-56]. In addition, anxiety related disorders and locomotor deficits are important negative outcome of TBI [6, 57]. The inventors measured spontaneous locomotor activities and anxiety disorder in mice following rTBI in the OF and the EPM. In the OF, rTBI mice spent more time and covered longer distances in the CZ of, the zone that is considered anxiogenic for mice. Similarly, on the EPM, although mice hardly entered the open arm, they explored the CZ significantly more compared to the sham mice. Thus, consistent with other studies [58,59] the rTBI mice showed hyperactivity, poor judgement and increased risk-taking behaviors also observed in human CTE patients [54, 60]. In addition, increased freezing episodes in the CZ of shows increases anxiety in the mice. The inventors also observed significant deficiency in motor coordination on the rotarod in the rTBI mice. Following shcombo or shcombo+hMSC treatments these behavioral deficiencies were improved significantly showing the treatment efficacy, with shcombo+hMSC treatment showing equal or increased efficiency in improving the behavioral deficiencies.

Example 5—Prophetic Example

A 28 year old male patient presents with headaches, nausea, sensory problems, confusion, anxiety and memory problems after a falling off a ladder and hitting his head on the ground. A diagnosis of traumatic brain injury (TBI) is made.

Dendrimers are manufactured as discussed in Example 1. Briefly, miR30-shRNA knockdown vectors for downregulating CCL20 and CCR6 are used and each vector is encoded with 4 inserts of shRNA (CCL20 and CCR6) sequence with (pRP[miR30-shRNA]-Neo-CMV>TurboRFP) CMV promoter, turbo RFP reporter and ampicillin as selectable marker gene. The plasmids are cloned and amplified in DH5alpha competent cells. The plasmids are isolated using a mega preparation plasmid isolation kit from Qiagen (Maryland, USA).

Dendriplexes are formed as described in Example 2. Briefly, PAMAM dendrimer and TurboRFP-pDNA expressing shRNAs, prepared as noted above, are complexed via electrostatic interactions to form PAMAM/DNA dendriplexes. The plasmid DNA-dendrimer complexation is achieved by adding plasmid DNA to dendrimer, at a final nitrogen-to-phosphate (N/P) ratio of 10, followed by vigorous vortexing for 1 minute.

A therapeutically effective amount of at least one million human mesenchymal stem cells (hMSCs) is prepared.

The patient is simultaneously administered a therapeutically effective amount of the dendriplexes both intranasally and intravenously. After administration of the dendriplexes, the patient is administered the therapeutically effective amount of hMSCs intranasally. The patient is evaluated one week after administration for improvement of symptoms. The patient shows improvement both cognitively as well as physically. If improvement of symptoms is not shown, an additional dose of both dendriplexes and hMSCs is administered.

CONCLUSION

In summary, rTBI in mice causes neurodegeneration, neuroinflammation including expression of proinflammatory chemokine CCL20 and behavioral deficits. Nanoparticle mediated silencing of CCL20 and its sole receptor CCR6 reduces the inflammation. hMSC treatment reduces the inflammation and increases the BDNF expression indicating a pre-reparative stage. Treatment with shcombo prior to hMSC transplantation significantly improves the efficacy of hMSC and behavioral deficits. The inventors have developed a therapeutic system that can be adopted as effective regenerative therapy for rTBI.

REFERENCES

1. Peterson, A. B., Xu Likang, Daugherty, Jill, Breiding, Matthew J., *Surveillance Report of Traumatic Brain Injury-related Emergency Department Visits, Hospitalizations, and Deaths—United States,* 2014. Survillance Report, Centers for Disease Control and Prevention, U. S. Department of Health and Human Services., 2019: p. 1-23.
2. Draper, K. and J. Ponsford, *Cognitive functioning ten years following traumatic brain injury and rehabilitation.* Neuropsychology, 2008. 22(5): p. 618-625.
3. Ponsford, J., K. Draper, and M. Schonberger, *Functional outcome 10 years after traumatic brain injury: its relationship with demographic, injury severity, and cognitive and emotional status.* J Int Neuropsychol Soc, 2008. 14(2): p. 233-42.
4. Lindquist, L. K., H. C. Love, and E. B. Elbogen, *Traumatic Brain Injury in Iraq and Afghanistan Veterans: New Results From a National Random Sample Study.* J Neuropsychiatry Clin Neurosci, 2017. 29(3): p. 254-259.
5. Bryan, C. J. and T. A. Clemans, *Repetitive traumatic brain injury, psychological symptoms, and suicide risk in a clinical sample of deployed military personnel.* JAMA Psychiatry, 2013. 70(7): p. 686-91.
6. Popovitz, J., S. P. Mysore, and H. Adwanikar, *Long-Term Effects of Traumatic Brain Injury on Anxiety-Like Behaviors in Mice: Behavioral and Neural Correlates.* Front Behav Neurosci, 2019. 13: p. 6.
7. Hoge, C. W., et al., *Mild traumatic brain injury in U. S. Soldiers returning from Iraq.* N Engl J Med, 2008. 358(5): p. 453-63.
8. Terrio, H., et al., *Traumatic brain injury screening: preliminary findings in a US Army Brigade Combat Team.* J Head Trauma Rehabil, 2009. 24(1): p. 14-23.
9. Wojcik, B. E., et al., *Traumatic brain injury hospitalizations of U. S. army soldiers deployed to Afghanistan and Iraq.* Am J Prev Med, 2010. 38(1 Suppl): p. S108-16.
10. McKee, A. C. and M. E. Robinson, *Military-related traumatic brain injury and neurodegeneration.* Alzheimers Dement, 2014. 10(3 Suppl): p. S242-53.
11. Carbonara, M., et al., *Neuroprotection in Traumatic Brain Injury: Mesenchymal Stromal Cells can Potentially Overcome Some Limitations of Previous Clinical Trials.* Front Neurol, 2018. 9: p. 885.
12. Cox, C. S., Jr., J. Juranek, and S. Bedi, *Clinical trials in traumatic brain injury: cellular therapy and outcome measures.* Transfusion, 2019. 59 (S1): p. 858-868.
13. Nichol, A., et al., *Erythropoietin in traumatic brain injury (EPO-TBI): a double-blind randomised controlled trial.* Lancet, 2015. 386(10012): p. 2499-506.
14. Robertson, C. S., et al., *Effect of erythropoietin and transfusion threshold on neurological recovery after traumatic brain injury: a randomized clinical trial.* JAMA, 2014. 312(1): p. 36-47.
15. Skolnick, B. E., et al., *A clinical trial of progesterone for severe traumatic brain injury.* N Engl J Med, 2014. 371(26): p. 2467-76.
16. Galindo, L. T., et al., *Mesenchymal stem cell therapy modulates the inflammatory response in experimental traumatic brain injury.* Neurol Res Int, 2011. 2011: p. 564089.
17. Parr, A. M., C. H. Tator, and A. Keating, *Bone marrow-derived mesenchymal stromal cells for the repair of central nervous system injury.* Bone Marrow Transplant, 2007. 40(7): p. 609-19.
18. Redondo-Castro, E., et al., *Interleukin-1 primes human mesenchymal stem cells towards an anti-inflammatory and pro-trophic phenotype in vitro.* Stem Cell Res Ther, 2017. 8(1): p. 79.
19. Garcia-Olmo, D., et al., *A phase I clinical trial of the treatment of Crohn's fistula by adipose mesenchymal stem cell transplantation.* Dis Colon Rectum, 2005. 48(7): p. 1416-23.
20. Das, M., et al., *Lateral fluid percussion injury of the brain induces CCL20 inflammatory chemokine expression in rats.* J Neuroinflammation, 2011. 8: p. 148.
21. Das, M., et al., *CCL20-CCR6 axis modulated traumatic brain injury-induced visual pathologies.* J Neuroinflammation, 2019. 16(1): p. 115.
22. Leonardo, C. C., et al., *CCL20 Is Associated with Neurodegeneration Following Experimental Traumatic Brain Injury and Promotes Cellular Toxicity In Vitro.* Transl Stroke Res, 2012. 3(3): p. 357-63.
23. Das, M., et al., *Pioglitazone treatment prior to transplantation improves the efficacy of human mesenchymal stem cells after traumatic brain injury in rats.* Sci Rep, 2019. 9(1): p. 13646.
24. Mastorakos, P., et al., *Hydroxyl PAMAM dendrimer-based gene vectors for transgene delivery to human retinal pigment epithelial cells.* Nanoscale, 2015. 7(9): p. 3845-56.
25. Mastorakos, P., et al., *Biodegradable brain-penetrating DNA nanocomplexes and their use to treat malignant brain tumors.* J Control Release, 2017. 262: p. 37-46.
26. Das, M., et al., *Mesenchymal stem cell therapy for the treatment of traumatic brain injury: progress and prospects.* Rev Neurosci, 2019. 30(8): p. 839-855.
27. Gurkoff, G., et al., *Voltage-gated calcium channel antagonists and traumatic brain injury.* Pharmaceuticals (Basel), 2013. 6(7): p. 788-812.

28. Narayan, R. K., et al., *Clinical trials in head injury*. J Neurotrauma, 2002. 19(5): p. 503-57.

29. Aminmansour, B., et al., *The efficacy of Cyclosporine-A on Diffuse Axonal Injury after Traumatic Brain Injury*. Adv Biomed Res, 2014. 3: p. 35.

30. Del Zoppo, G. J. and M. A. Moskowitz, *Translating interventions from ischemic stroke models to patients: the view in 2009*. Front Neurol Neurosci, 2009. 25: p. 34-38.

31. Hall, E. D., R. A. Vaishnav, and A. G. Mustafa, *Antioxidant therapies for traumatic brain injury*. Neurotherapeutics, 2010. 7(1): p. 51-61.

32. Morris, G. F., et al., *Failure of the competitive N-methyl-D-aspartate antagonist Selfotel (CGS 19755) in the treatment of severe head injury: results of two phase III clinical trials. The Selfotel Investigators*. J Neurosurg, 1999. 91(5): p. 737-43.

33. Chen, S. F., et al., *Lovastatin improves histological and functional outcomes and reduces inflammation after experimental traumatic brain injury*. Life Sci, 2007. 81(4): p. 288-98.

34. Schutyser, E., S. Struyf, and J. Van Damme, *The CC chemokine CCL20 and its receptor CCR6*. Cytokine Growth Factor Rev, 2003. 14(5): p. 409-26.

35. Qi, W., et al., *The roles of Kruppel-like factor 6 and peroxisome proliferator-activated receptor-gamma in the regulation of macrophage inflammatory protein-3alpha at early onset of diabetes*. Int J Biochem Cell Biol, 2011. 43(3): p. 383-92.

36. Seyhan, A. A., *RNAi: a potential new class of therapeutic for human genetic disease*. Hum Genet, 2011. 130(5): p. 583-605.

37. Sah, D. W., *Therapeutic potential of RNA interference for neurological disorders*. Life Sci, 2006. 79(19): p. 1773-80.

38. Yang, H., *Nanoparticle-mediated brain-specific drug delivery, imaging, and diagnosis*. Pharm Res, 2010. 27(9): p. 1759-71.

39. Kannan, S., et al., *Dendrimer-based postnatal therapy for neuroinflammation and cerebral palsy in a rabbit model*. Sci Transl Med, 2012. 4(130): p. 130ra46.

40. Kim, I. D., et al., *Neuroprotection by biodegradable PAMAM ester (e-PAM-R)-mediated HMGB1 siRNA delivery in primary cortical cultures and in the postischemic brain*. J Control Release, 2010. 142(3): p. 422-30.

41. Kambhampati, S. P., et al., *Intracellular delivery of dendrimer triamcinolone acetonide conjugates into microglial and human retinal pigment epithelial cells*. Eur J Pharm Biopharm, 2015. 95 (Pt B): p. 239-49.

42. Karolczak, K., et al., *Poly(amido)amine dendrimers generation 4.0 (PAMAM G4) reduce blood hyperglycaemia and restore impaired blood-brain barrier permeability in streptozotocin diabetes in rats*. Int J Pharm, 2012. 436(1-2): p. 508-18.

43. Lee, J. H., et al., *Polyplexes assembled with internally quaternized PAMAM-OH dendrimer and plasmid DNA have a neutral surface and gene delivery potency*. Bioconjug Chem, 2003. 14(6): p. 1214-21.

44. Albertazzi, L., et al., *In vivo distribution and toxicity of PAMAM dendrimers in the central nervous system depend on their surface chemistry*. Mol Pharm, 2013. 10(1): p. 249-60.

45. Shakhbazau, A., et al., *Use of polyamidoamine dendrimers to engineer BDNF-producing human mesenchymal stem cells*. Mol Biol Rep, 2010. 37(4): p. 2003-8.

46. Win-Shwe, T. T., et al., *Effects of PAMAM dendrimers in the mouse brain after a single intranasal instillation*. Toxicol Lett, 2014. 228(3): p. 207-15.

47. Wagner, B., et al., *Neuronal survival depends on EGFR signaling in cortical but not midbrain astrocytes*. EMBO J, 2006. 25(4): p. 752-62.

48. Sofroniew, M. V., *Molecular dissection of reactive astrogliosis and glial scar formation*. Trends Neurosci, 2009. 32(12): p. 638-47.

49. Hasan, A., et al., *Mesenchymal Stem Cells in the Treatment of Traumatic Brain Injury*. Front Neurol, 2017. 8: p. 28.

50. Phatnani, H. and T. Maniatis, *Astrocytes in neurodegenerative disease*. Cold Spring Harb Perspect Biol, 2015. 7(6).

51. Rojas, M., et al., *Bone marrow-derived mesenchymal stem cells in repair of the injured lung*. Am J Respir Cell Mol Biol, 2005. 33(2): p. 145-52.

52. McKee, A. C., et al., *Chronic traumatic encephalopathy in athletes: progressive tauopathy after repetitive head injury*. J Neuropathol Exp Neurol, 2009. 68(7): p. 709-35.

53. Ojo, J. O., et al., *Repetitive mild traumatic brain injury augments tau pathology and glial activation in aged hTau mice*. J Neuropathol Exp Neurol, 2013. 72(2): p. 137-51.

54. Omalu, B., et al., *Emerging histomorphologic phenotypes of chronic traumatic encephalopathy in American athletes*. Neurosurgery, 2011. 69(1): p. 173-83; discussion 183.

55. Omalu, B. I., et al., *Chronic traumatic encephalopathy, suicides and parasuicides in professional American athletes: the role of the forensic pathologist*. Am J Forensic Med Pathol, 2010. 31(2): p. 130-2.

56. Omalu, B. I., et al., *Chronic traumatic encephalopathy in a national football league player: part II*. Neurosurgery, 2006. 59(5): p. 1086-92; discussion 1092-3.

57. Petraglia, A. L., et al., *The spectrum of neurobehavioral sequelae after repetitive mild traumatic brain injury: a novel mouse model of chronic traumatic encephalopathy*. J Neurotrauma, 2014. 31(13): p. 1211-24.

58. Laviola, G., et al., *Risk-taking behavior in adolescent mice: psychobiological determinants and early epigenetic influence*. Neurosci Biobehav Rev, 2003. 27(1-2): p. 19-31.

59. Toledo-Rodriguez, M. and C. Sandi, *Stress during Adolescence Increases Novelty Seeking and Risk-Taking Behavior in Male and Female Rats*. Front Behav Neurosci, 2011. 5: p. 17.

60. McKee, A. C., et al., *The spectrum of disease in chronic traumatic encephalopathy*. Brain, 2013. 136 (Pt 1): p. 43-64.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

It is also to be understood that the following claims are intended to cover all of the generic and specific features of the invention herein described, and all statements of the scope of the invention that, as a matter of language, might be said to fall therebetween.

What is claimed is:

1. A therapeutic system to increase efficacy of human mesenchymal stem cells (hMSCs) to treat traumatic brain injury (TBI) in a patient in need thereof, comprising:

at least one PAMAM/DNA dendriplex and a pharmaceutically acceptable carrier, the at least one PAMAM/DNA dendriplex consisting of:

at least one modified polyamidoamine (PAMAM) dendrimer nanoparticle modified by using extrusion to remove large particles to obtain a size of about 5 nm with 0.150 polydispersity index; and at least one short hairpin RNA (shRNA)-encoding DNA plasmid complexed via electrostatic interactions to an outer surface of the at least one modified PAMAM dendrimer nanoparticle by vigorous vortexing to form at least one PAMAM/DNA dendriplex; and a therapeutically effective amount of the hMSCs;

wherein the at least one plasmid DNA and the at least one modified PAMAM are complexed at a final nitrogen to phosphate (N/P) ratio of 10;

wherein the at least one shRNA-encoding DNA plasmid comprises a nucleotide sequence encoding at least one shRNA targeting chemokine ligand 20 (CCL20) and at least one shRNA targeting chemokine receptor 6 (CCR6);

wherein the therapeutically effective amount of hMSCs are administered to the patient in need thereof subsequently to at least one administration of the at least one PAMAM/DNA dendriplex.

2. The therapeutic system of claim 1, wherein the PAMAM/DNA dendriplex is administered to the patient more than once.

3. The therapeutic system of claim 1, wherein size of the at least one dendriplex is about 100 nm.

4. A method of enhancing efficacy of human mesenchymal stem cells (hMSCs) to treat a traumatic brain injury (TBI) by prior gene silencing in a patient in need thereof, comprising:

administering at least two PAMAM/DNA dendriplexes to the patient in need thereof at least once, each of the at least two PAMAM/DNA dendriplexes consisting of:

at least one modified polyamidoamine (PAMAM) dendrimer nanoparticle modified by using extrusion to remove large particles to obtain a size of about 5 nm with 0.150 polydispersity index; and at least one short hairpin RNA (shRNA)-encoding DNA plasmid complexed via electrostatic interactions to an outer surface of the at least one modified PAMAM dendrimer nanoparticle by vigorous vortexing;

wherein the at least one plasmid DNA and the at least one modified PAMAM dendrimer are complexed at a final nitrogen to phosphate (N/P) ratio of 10; and subsequently administering a therapeutically effective amount of hMSCs to the patient in need thereof;

wherein the at least one shRNA-encoding DNA plasmid comprises a nucleotide sequence encoding at least one shRNA targeting chemokine ligand 20 (CCL20) and at least one shRNA targeting chemokine receptor 6 (CCR6).

5. The method of claim 4, wherein the at least one PAMAM/DNA dendriplex is administered more than once and the therapeutically effective amount of hMSCs is administered after at least one of the administrations of the at least one PAMAM/DNA dendriplex.

6. The method of claim 4, wherein the at least one PAMAM/DNA dendriplex is administered intranasally and at least one PAMAM/DNA dendriplex is administered intravenously.

7. The method of claim 4, wherein brain derived neurotrophic factor (BDNF) is synergistically increased as compared to a control.

8. The method of claim 4, wherein anxiety induced by TBI is reduced.

9. A method of synergistically increasing brain derived neurotrophic factor (BDNF) in a patient following traumatic brain injury (TBI) comprising:

administering at least once to the patient at least two PAMAM/DNA dendriplexes, each of the at least two PAMAM/DNA dendriplexes consisting of:

at least one modified polyamidoamine (PAMAM) dendrimer nanoparticle modified by using extrusion to remove large particles to obtain a size of about 5 nm with 0.150 polydispersity index; and at least one short hairpin RNA (shRNA)-encoding DNA plasmid complexed via electrostatic interactions to an outer surface of the at least one modified PAMAM dendrimer nanoparticle by vigorous vortexing;

wherein the at least one plasmid DNA and the at least one modified PAMAM are complexed at a final nitrogen to phosphate (N/P) ratio of 10;

subsequently administering a therapeutically effective amount of human mesenchymal stem cells (hMSCs) to the patient;

wherein the at least one shRNA-encoding DNA plasmid comprises a nucleotide sequence encoding at least one shRNA targeting chemokine ligand 20 (CCL20) and at least one shRNA targeting chemokine receptor 6 (CCR6);

wherein at least one dendriplex is administered intranasally and at least one dendriplex is administered intravenously.

* * * * *